(12) United States Patent
Lamb et al.

(10) Patent No.: US 6,191,258 B1
(45) Date of Patent: Feb. 20, 2001

(54) PURIFIED PALINDROMIC ELEMENT BINDING FACTOR

(75) Inventors: Christopher J. Lamb; Peter Doerner, both of San Diego, CA (US); Goetz Laible, Vienna (AT)

(73) Assignee: The Salk Institute for Biological Studies, La Jolla, CA (US)

( * ) Notice: Under 35 U.S.C. 154(b), the term of this patent shall be extended for 0 days.

(21) Appl. No.: 09/189,344

(22) Filed: Nov. 10, 1998

Related U.S. Application Data

(62) Division of application No. 08/669,721, filed on Jun. 27, 1996, now Pat. No. 5,834,236.

(51) Int. Cl.[7] .................................................. C07K 14/415
(52) U.S. Cl. ............................................................. 530/350
(58) Field of Search ................................... 530/300, 324, 530/350

(56) References Cited

PUBLICATIONS

Cramer, et al., Phenylalanine ammonia–lyase gene organization and structure, Plant Molecular Biology, vol. 12:367–383, 1989.

Tjaden, et al., A Novel AT–Rich DNA Binding Protein That Combines an HMG I–like DNA Binding Domain . . . , The Plant Cell, vol. 6: 107–118, Jan. 1994.

*Primary Examiner*—Terry McKelvey
(74) *Attorney, Agent, or Firm*—Gray Cary Ware & Freidenrich LLP; Lisa A. Haile

(57) ABSTRACT

A novel transcription enhancer element, $(AATT)_n$, that increases the activity of cis-elements in heterologous promoter constructs without altering their intrinsic specificity is provided. Also provided is a transcription factor, PABF, which specifically binds to the (AATT) repeat element and methods of use therefor.

3 Claims, 14 Drawing Sheets

```
  1  CTGAATTTCACCATTTCTGTATCTTCACAAAGCTTATTTGTAAATTACATACATGCCCTG   60

61  ATGGACCCATCCATGGATCTACCGACGACCACCGAATCACCGACGTTTAACTCAGCTCAA  120
  1   M  D  P  S  M  D  L  P  T  T  T  E  S  P  T  F  N  S  A  Q   20

121  GTTGTAAACCATGCTCCTACCCCTACCCCTCCTCAACCCCCTCCCCCTGCCCCTTCCTTT  180
 21   V  V  N  H  A  P  T  P  T  P  P  Q  P  P  P  P  A  P  S  F   40

181  TCGCCTACCCACCCGCCTTATGCTGAGATGATAACGGCGGCGATAACGGCGTTAAAGGAG  240
 41   S  P  T  H  P  P  Y  A  E  M  I  T  A  A  I  T  A  L  K  E   60

241  AGGGATGGGTCAAGCAGGATAGCCATAGCTAAGTACATAGACCGAGTCTACACAAATCTT  300
 61   R  D  G  S  S  R  I  A  I  A  K  Y  I  D  R  V  Y  T  N  L   80

301  CCACCGAATCACTCGGCCCTGTTGACTCACCATCTTAAGCGTTTGAAGAACAGTGGTTAC  360
 81   P  P  N  H  S  A  L  L  T  H  H  L  K  R  L  K  N  S  G  Y  100

361  CTTGCTATGGTCAAACACTCTTACATGCTCGCCGGACCACCTGGATCTGCTCCTCCGCCT  420
101   L  A  M  V  K  H  S  Y  M  L  A  G  P  P  G  S  A  P  P  P  120

421  CCTTCCGCCGACGCCGATTCCAACGGTGTTGGTACTGATGTTTCTTCTCTTTCTAAAAGG  480
121   P  S  A  D  A  D  S  N  G  V  G  T  D  V  S  S  L  S  K  R  140

481  AAACCTGGTCGTCCTCCTAAGCTCAAGCCTGAGGCCCAACCTCATGCTCAGCCTCAAGTC  540
141   K  P  G  R  P  P  K  L  K  P  E  A  Q  P  H  A  Q  P  Q  V  160

541  CAAGCTCAAGTCCAATTTCAAGACCAATTCCAAGCTCAGCTTCAAGCCCAGCTTCAAGCC  600
161   Q  A  Q  V  Q  F  Q  D  Q  F  Q  A  Q  L  Q  A  Q  L  Q  A  180

601  CAACTTCAAGCCCAACAGCAGCAAGCAGCCCAGTTTCAACCTCAATTCCAACTCATCCAA  660
181   Q  L  Q  A  Q  Q  Q  Q  A  A  Q  F  Q  P  Q  F  Q  L  I  Q  200

661  CAACAGCCCCAGTACTTACCTCAACAACAGTTCCAGCCCGACCCATTACTCCAACCTCAG  720
201   Q  Q  P  Q  Y  L  P  Q  Q  Q  F  Q  P  D  P  L  L  Q  P  Q  220

721  CAACAGTTCCAGACCCAGCCACAGACGCAGGCCTATGCTACTCCTGAAGGCCATAATTAT  780
221   Q  Q  F  Q  T  Q  P  Q  T  Q  A  Y  A  T  P  E  G  H  N  Y  240

781  GCTGGCCTTGGCGCTGAATCCGTGTTTGTTTCTCTTGGGCTAGCTGATGGGCCTGTTGGA  840
241   A  G  L  G  A  E  S  V  F  V  S  L  G  L  A  D  G  P  V  G  260
```

FIG. 5A

```
     841 GTTCAGAATCCTGCTGTTGGGCTGGCTCCGGCACCGGGAGCTGAAGAGAGTACGGCAAAG  900
     261  V  Q  N  P  A  V  G  L  A  P  A  P  G  A  E  E  S  T  A  K   280

901 AGACGACCAGGTCGTCCCCGTAAGGATGGTTCCACTGTGGTTAAACCGGTGGAACCCAAA  960
     281  R  R  P  G  R  P  R  K  D  G  S  T  V  V  K  P  V  E  P  K   300

961 TTACCGGACCAGAGCGGTGGTAGTAAGAGGAGACCTGGTCGTCCTCCTAAGAGTGTGACA 1020
     301  L  P  D  Q  S  G  G  S  K  R  R  P  G  R  P  P  K  S  V  T   320

1021 GTTAATGCTGCTCCTGGATCAGCTATGGGTTCTGGACGACGAGGTCGGCCCAGGAAAAAT 1080
     321  V  N  A  A  P  G  S  A  M  G  S  G  R  R  G  R  P  R  K  N   340

1081 TCTGTTCCTGGACGACGAGGTCGGCCCAGGAAGAATGCGGCTGTTGCTGCTGCCAATGGC 1140
     341  S  V  P  G  R  R  G  R  P  R  K  N  A  A  V  A  A  A  N  G   360

1141 GGTGCCAATGTCGCAAATATTCCTTCTGTTGGTGCCAATGTGACCAATGTTCCAGCTGGT 1200
     361  G  A  N  V  A  N  I  P  S  V  G  A  N  V  T  N  V  P  A  G   380

1201 GGTGTCCCGGGAGCCATAACAACACCTAAACGAAGGGGACGGCCACCAAGGTCTAGTGGA 1260
     381  G  V  P  G  A  I  T  T  P  K  R  R  G  R  P  P  R  S  S  G   400

1261 CCTCCTGCTGCTACTGTGGGTGTTACAGATGTGCCTATTGCTGCTGCTTTTGATACGGAA 1320
     400  P  P  A  A  T  V  G  V  T  D  V  P  I  A  A  A  F  D  T  E   420

1321 AACTTGCCTAATGCTGTTGGTGGTGGCGGTGTCACAAATAATGGGGCTCTGCCTCCCCTC 1380
     421  N  L  P  N  A  V  G  G  G  G  V  T  N  N  G  A  L  P  P  L   440

1381 GGAAAGCGACGTGGACGGCCTCCAAAATCTTACGGCGCTGCAGCCGCTGCTCCTACTGTT 1440
     441  G  K  R  R  G  R  P  P  K  S  Y  G  A  A  A  A  A  P  T  V   460

1441 AAGAGACCCAGGAAGCTTTCTGGAAAACCTCTGGGTCGACCTAGAAAGAATGTGACATCC 1500
     461  K  R  P  R  K  L  S  G  K  P  L  G  R  P  R  K  N  V  T  S   480

1501 CCTGCAGTTTCGGACCCCAAGTTGGTGGTGGCCTATGAAGAGCTAAAGGGGAAACTTGAA 1560
     481  P  A  V  S  D  P  K  L  V  V  A  Y  E  E  L  K  G  K  L  E   500

1561 CACATGCAATCAAGGAATCAAGGAAGCAGCGAATGCGCTGAAGCCATGCTTAAATGCTGAA 1620
     501  H  M  Q  S  R  I  K  E  A  A  N  A  L  K  P  C  L  N  A  E   520
```

FIG. 5B

```
1621 TCGCCAGCAATTGCTCTGGCAGCATTGCAAGAGTTAGAAGAGTTAGCAGCAGCAGGGGGG 1680
 521   S  P  A  I  A  L  A  A  L  Q  E  L  E  E  L  A  A  A  G  G   540

1681 AATCCAGTGCAGCAAAATTGATAAAAGAAGATGTCGCAGAGATTAGGAATATGGAGGCAG 1740
 541   N  P  V  Q  Q  N  *                                            546

1741 TGCTTAAACTCAGAGTGTTAAACATTATTCAAGGCTGGAAACCATGAAAATCAAGGAAGT 1800

1801 TTCGGTGCAGACTAGTGTTTGTGACAGGACGAAGATGCGCTTAGACTTGGAGGCAGTGTA 1860

1861 GCTACCTACCTCTAATGTCAATTTGTTAGGTTAAAGCAGGATTTGATATTTTGTTGCACA 1920

1921 GTATGAAGTATGTTTTAGTTCTAACTGTATTAGCAGTTGATTTCGTCATTTGATAATTAC 1980

1981 CTTATTCTGCTAATTTGGTTAATGACAATTAAGGGGGAGACAAAATCATGCTCGTGGGCT 2040

2041 ATATGTACTGTTGTTTGAGTATGTTGAATGGATGGAAATGCCTTTGTTAGATAGATGTAT 2100

2101 AATGCCGGCATTATCCCTCATCAACAGTTGCCTTTGCAAATGTCGTAAAAGCATTTGAAT 2160

2161 TTTAT                                                         2165
```

FIG. 5C

```
PABF:                    35  PPAPSFSPTHPPYAEMITAAITALKERDGSSRIAIAKYIDRVYTN

A.thaliana, H1.2         53  P   ++HP Y EMI    AI   LKER GSS+ AI  K+I+   +
L.esculentum, H1         47  P  S+PTHPPY EMI   AI   LKER GSS+ AI  K+I+   +
A.thaliana, H1.1         29      +HP Y EMI     AI   LKER GSS+ AI  K+I+   +
A.thaliana, H1.1.        61      +HP Y EMI     AI   LKER GSS+ AI  K+I+
P.sativum, H1            56      +HP Y EMI     AI  +LKE++GSS+ AIAK+I+
V.carteri, H1-1          48  P  +PTHPPY EM+    AIT +LKER+GSS A+ K+I+
Z.mays, H1               43  P   SPTH PYAEM++  AIT+LKER GSS  AIAK+++     Y PABF:                        LPPNHSALLTHHLKRLKNSGYLAMVKHSYMLAGPPGSAPPPPSA      123

A.thaliana, H1.2             LL  +LKRL   S  L  VK S+  +    +A P  P+A          141
L.esculentum, H1             LP N LK+    S  L  VK+SY L                        122
A.thaliana, H1.1             LL  +LKRL   SG L  VK S+ L       A  P  +A         109
A.thaliana, H1.1.            LL  +LKRL   SG L  VK S+ L       A  P  +A         141
P.sativum, H1                LP N +LK+    SG L  VK S+ L+      A  P  +A         129

FIG. 7A
```

| AT-hook | TPKRPRGRPPK | |
|---|---|---|
| HMG-Y, a | -----G-----R- | (21) |
| HMG-Y, b | ---------KG | (42) |
| HMG-Y, c | PGRK-----K- | (68) |
| PABF, a | -A--RP---R- | (278) |
| PABF, b | GS--RP----- | (307) |
| PABF, c | MGSGR----R- | (329) |
| PABF, d | SVPGR----R- | (344) |
| PABF, e | -TPKR-----R | (387) |
| PABF, f | PLGKR------ | (439) |
| PABF, g-1 | -V---- | (459) |
| PABF, g-2 | ---R- | (472) |

FIG. 7B

PURIFIED PALINDROMIC ELEMENT BINDING FACTOR

This is a divisional of U.S. application Ser. No. 08/669,721, filed Jun. 27, 1996, now U.S. Pat. No. 5,834,236.

FIELD OF THE INVENTION

The present invention relates generally to gene expression and specifically to a novel enhancer element that increases the rate of transcription of a gene operably linked thereto, particularly in plants.

BACKGROUND OF THE INVENTION

Genes are regulated in an inducible, cell type-specific or constitutive manner. There are different types of structural elements which are involved in the regulation of gene expression. Cis-acting elements, located in the proximity of, or within genes, serve to bind sequence-specific DNA binding proteins, i.e., trans-acting factors. The binding of proteins to DNA is responsible for the initiation, maintenance, or down-regulation of gene transcription.

Cis-acting elements which control genes include promoters, enhancers and silencers. Promoters are positioned next to the transcription start site and function in an orientation-dependent manner, while enhancer and silencer elements, which modulate the activity of promoters, may be flexible with respect to their orientation and distance from the transcription start site.

An example of a specifically regulated gene in plants is phenylalanine ammonia-lyase (PAL), which catalyzes the deamination of phenylalanine to cinnamic acid, the precursor of a wide variety of natural products based on the phenylpropane skeleton. During vascular development, PAL is selectively expressed in differentiating xylem cells associated with deposition of the structural polymer lignin. Lignin, the second most abundant biopolymer after cellulose, is the major structural cell wall component of cells forming vessels in plant tissue (xylem). The xylem is responsible for movement of water and inorganic solutes from plant roots to plant shoots. PAL genes are expressed at correspondingly high levels in differentiating xylem.

The ability to artificially regulate the rate of gene expression provides a means of producing plants with new characteristics. There are numerous situations in which increased levels of gene expression, including increased endogenous gene expression, may be desirable. Such situations include, for example, production of protein plant products for agricultural or commercial purposes.

SUMMARY OF THE INVENTION

The present invention provides a novel repeat element which functions as a non-specific enhancer. In other words, the invention enhancer element does not affect the intrinsic specificity of a promoter associated with the enhancer element. Instead, the enhancer element boosts the activity of the promoter thereby resulting in a desired level of expression of a gene associated with the promoter. A novel transcription factor, palindromic element binding factor (PABF), which binds to the novel repeat element is also provided.

In a first embodiment, the invention provides an enhancer element comprising an isolated nucleotide sequence consisting of at least the sequence $(AATT)_n$, where $n \geq 2$, and preferably from about 2 to about 20. The sequence $(AATT)_n$ has cis-acting, non-specific, enhancer activity. In one aspect, the invention provides a method for increasing expression of a gene in a cell comprising operably linking a $(AATT)_n$ repeat element to a heterologous promoter which is operably linked with the gene, thereby permitting increased expression of the gene.

In another embodiment, the invention provides a substantially purified palindromic element binding factor (PABF) polypeptide characterized as having a molecular weight of approximately 67 kDa, as determined by SDS-PAGE, binding to a $(AATT)_n$ repeat element, where $n \geq 2$, and having a H1 histone domain, a glutamine rich domain and a high mobility group (HMG) I/Y domain. PABF acts as a transcription factor and binds to the (AATT) repeat element of the invention.

BRIEF DESCRIPTION OF THE DRAWING

FIGS. 5a and 5b show the nucleotide and deduced amino acid sequence of the PABF cDNA (SEQ ID NO:2 and 3, respectively). The deduced amino acid sequence, shown in the one-letter code, starts with the first methione of the open reading frame at position 61 and terminates at the stop codon following N-546. The arrows indicate the 5' and 3'-end of the originally isolated truncated cDNA clone. The AT-hook motifs are underlined.

FIG. 7A is a comparison of sequence homology of domains of PABF with plant histone H1 genes and the HMG I/Y DNA-binding motif (AT hook) (SEQ ID NOS:9–15). Conservative amino acid substitutions are indicated by a + sign.

FIG. 7B shows the repeated dA·dT-DNA binding modules of the mammalian HMG I/Y proteins (a–c) (SEQ ID NOS:17–22). Similar repeated sequences have been found in PABF SEQ ID NO:3 (a–g). Only the amino acids differing from the consensus AT-hook motif are indicated. The invariant core motif RGRP is printed in bold. Numbers in brackets indicate the amino acid position within the respective protein.

DESCRIPTION OF THE PREFERRED EMBODIMENTS

Figures 1, 1A:
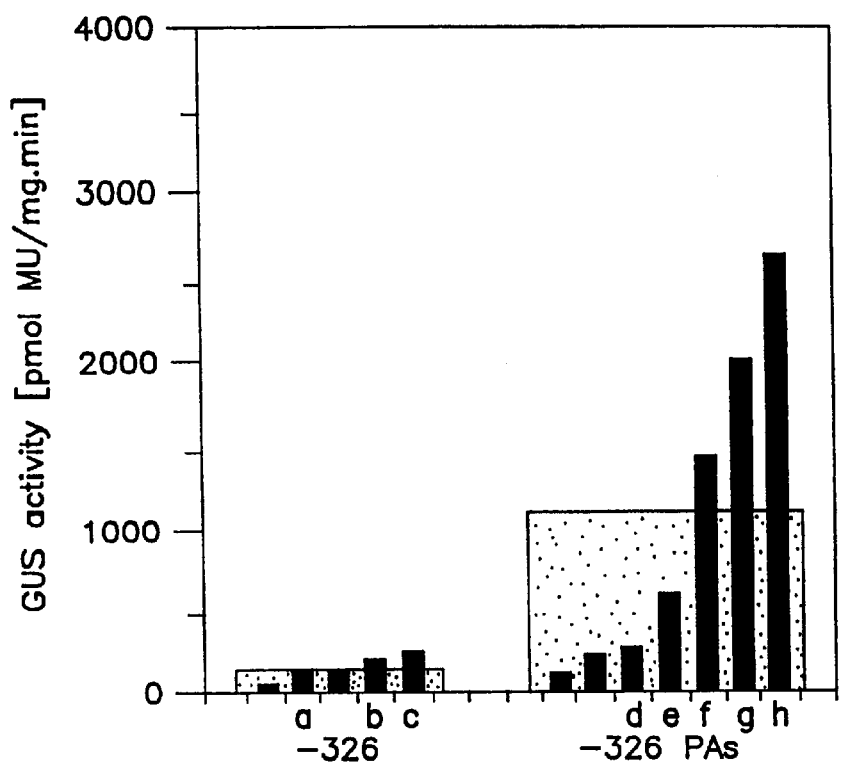
FIG. 1A shows a bar graph for GUS activity (mean of two plants for each transgenic line) in extracts of mature pigmented corolla (petal) tissue (panel a–d), unpigmented corolla tissue (panel f) and petioles above the fifth internode (panel e) from independent transformants containing the constructs illustrated in FIG. 1B. The shaded boxes represent the mean values of the GUS activities measured in independent transgenic lines. Letters in panel a and numbers in panel d indicate the transgenic lines from which the GUS data in panels e and f were derived.

The present invention provides a novel enhancer element and a novel palindromic element binding factor (PABF) that binds to the enhancer element. The invention enhancer element and binding factor provide a method for enhanced gene expression, particularly in plants.

PAL2 Enhancer element

The enhancer element of the present invention comprises a plurality of the isolated repetitive unit (AATT). The enhancer is minimally the number of repeated elements required for enhanced expression, usually not more than about two times the number of repetitive units present in the natural enhancer.

The (AATT) repeats, as described herein, may be imperfect, i.e., having a specific core sequence (AATT) together with some degree of variability in the total repetitive sequence. Enhancer elements of the invention may consist entirely of AATT repeats, of imperfect repeats, of a combination of AATT repeats and imperfect repeats.

The invention enhancer element has at least 2, preferably at least about 4, and most preferably at least about 8 repeats of the 4 bp sequence, and preferably no more than about 20 repeats of the 4 bp sequence. Therefore, the enhancer element will contain at least about 8 base pairs (bp), preferably about 16 bp to about 32 bp and most preferably no more than about 80 bp.

The invention enhancer element may be used in the same or different species from which it is derived or in which it naturally functions. A natural enhancer comprises a DNA sequence which in its native environment is generally upstream from and within about 600 bp of a promoter. The invention enhancer element is cis-acting and desirably is located within about 5000 bp, preferably about 2000 bp, and most preferably adjacent to or within about 1000 bp of the transcription initiation domain within the promoter to be enhanced. For example, if the initial nucleotide of the mRNA is designated +1, the sequence containing the enhancer is preferably located upstream from about −50 to about −1000 bp, usually from about −50 to −900, and more specifically from about −50 to about −800 bp. The enhancer element can be located upstream or downstream in relation to the promoter it enhances. Alternatively, the enhancer element may be positioned within introns in the transcription unit.

The enhancer element of the invention can be utilized with a variety of promoters, including promoters that are naturally found under control of the enhancer (homologous) as well as promoters not naturally associated with the enhancer region (heterologous).

Enhanced transcription in plants is useful in obtaining high levels of endogenous gene expression as well as high levels of exogenous gene expression. The term "endogenous" as used herein refers to a gene normally found in the wild-type host, while the term "exogenous" refers to a gene not normally found in the wild-type host.

The invention enhancer element is operably linked to a promoter which includes a transcription initiation domain. The term "transcription initiation domain" refers to a promoter having at least an RNA polymerase binding site and an mRNA initiation site. The promoter, in turn, is operably linked to a gene, endogenous or exogenous, which, when including an open reading frame (ORF) encodes a protein, and typically also includes the 5' and 3' untranslated sequences. Such open reading frames, or RNA encoding sequences include natural open reading frames encoding protein products; cDNA sequences derived from the mRNA; synthetic DNA; protein encoding sequences derived from exons of the natural gene (e.g., open reading frame produced by exon ligation); and/or combinations of the above. The appropriate transcription termination and polyadenylation sequences are also included.

Genes of interest, the level of expression of which may be increased according the present invention, include, for example, sequences from the natural genes (plant, animal, bacterial, viral, fungal) which encode primary RNA products; synthetic DNA sequences which encode a specific RNA or protein product; DNA sequences modified by mutagenesis, for example site specific mutagenesis; chimeras of any of the above (to produce fusion proteins); and DNA sequences encoding complementary RNA molecules (antisense), and combinations and/or fragments of the above.

Examples of proteins that can be produced at increased levels utilizing the presnet invention include, but are not limited to, nutritionally important proteins; growth promoting factors; proteins for early flowering in plants; proteins giving protection to the plant under certain environmental conditions, e.g., proteins conferring resistance to metals or other toxic substances, such as herbicides or pesticides; stress related proteins which confer tolerance to temperature extremes; proteins conferring resistance to fungi, bacteria, viruses, insects and nematodes; proteins of specific commercial value, e.g., enzymes involved in metabolic pathways, such as EPSP synthase.

The enhancer element described herein can be isolated from natural sources (e.g., phenylalanine ammonia-lyase (PAL)) or can be synthesized by standard DNA synthesis techniques (see for example, *Current Protocols in Molecular Biology*, Unit 2.11, eds. Ausubel, et al., John Wiley & Sons, 1995).

In one embodiment, the invention provides a method for increasing expression of a gene in a cell. The method includes operably linking a $(AATT)_n$ repeat element as described above, to a promoter operably linked to a gene of interest, and increasing expression of the gene. The promoter can be constitutive or inducible. The terms "increased" or "increasing" as used herein refer to gene expression which is elevated as compared to expression of the corresponding wild type gene that is not associated with a promoter containing an invention enhancer element.

The terms "operably associated" and "in operable linkage" refer to functional linkage between an enhancer element of the invention and a promoter sequence and also between a promoter sequence and the structural gene regulated by the promoter. The operably linked enhancer and promoter control the expression of the polypeptide encoded by the structural gene.

The expression of structural genes employed in the present invention may be driven by a number of promoters. Although the endogenous promoter of a structural gene of interest may be utilized herein for transcriptional regulation of the gene, preferably, the promoter is a foreign regulatory sequence. For plant expression vectors, suitable viral promoters include the 35S RNA and 19S RNA promoters of CaMV (Brisson, et al., *Nature*, 310:511, 1984; Odell, et al., *Nature*, 313:810, 1985); the full-length transcript promoter from Figwort Mosaic Virus (FMV) (Gowda, et al., *J. Biochem.*, 13D:301, 1989) and the coat protein promoter from TMV (Takamatsu, et al., *EMBO J.* 6:307, 1987). Alternatively, plant promoters such as the light-inducible promoter from the small subunit of ribulose bis-phosphate carboxylase (ssRUBISCO) (Coruzzi, et al., *EMBO J.*, 3:1671, 1984; Broglie, et al., *Science*, 224:838, 1984); mannopine synthase promoter (Velten, et al., *EMBO J.*, 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., *Mol. Cell. Biol.*, 6:559, 1986; Severin, et al., *Plant Mol. Biol.*, 15:827, 1990) may be used.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) employ an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.,* 90:4567, 1993); In2-1 and In2-2 regulator sequences which are activated by substituted benzenesulfonamides, e.g., herbicide safeners (Hershey, et al., *Plant Mol. Biol.,* 17:679, 1991); and the GRE regulatory sequences which are induced by glucocorticoids (Schena, et al., *Proc. Natl. Acad. Sci., U.S.A.,* 88:10421, 1991). Other promoters, both constitutive and inducible will be known to those of skill in the art.

The particular promoter selected should be capable of causing sufficient expression to result in the production of an effective amount of the structural gene product. The promoters used in the constructs of the present invention may be modified, if desired, to affect their control characteristics.

Environmentally regulated promoters, e.g., promoters regulated by light and drought may be utilized in the present invention. Hormonally regulated promoters may also be utilized.

Tissue specific promoters may also be utilized in the present invention. An example of a tissue specific promoter is the promoter expressed in shoot meristems (Atanassova, et al., *Plant J.,* 2:291, 1992). Other tissue specific promoters useful in transgenic plants, including fruit-specific and seed specific-promoters, or the cdc2a promoter and cyc07 promoter, will be known to those of skill in the art. (See for example, Ito, et al., *Plant Mol. Biol.,* 24:863, 1994; Martinez, et al., *Proc. Natl. Acad. Sci. USA,* 89:7360, 1992; Medford, et al., *Plant Cell,* 3:359, 1991; Terada, et al., *Plant Journal,* 3:241, 1993; Wissenbach, et al., *Plant Journal,* 4:411, 1993).

As discussed above, the enhancer element operably linked to the promoter utilized in the present invention will not alter the specificity of the promoter. In other words, the invention enhancer element does not affect the intrinsic specificity of the promoter associated with the enhancer element.

Optionally, a selectable marker may be associated with the construct containing the enhancer element and the structural gene operably linked to a promoter. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed plant cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II (kanamycin, neomycin and G418 resistance). Other suitable markers will be known to those of skill in the art. For example, screenable markers, such as the uidA gene, GUS, luciferase or the GFP gene may also be used.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" refers to alteration of the genotype of a host plant by the introduction of exogenous or endogenous nucleic acid sequences.

To commence a transformation process in accordance with the present invention, it is first necessary to construct a suitable vector and properly introduce the vector into the plant cell. The details of the construction of the vectors utilized herein are known to those skilled in the art of plant genetic engineering.

For example, the enhancer-promoter constructs utilized in the present invention can be introduced into plant cells using Ti plasmids, root-inducing (Ri) plasmids, and plant virus vectors. For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9, and Horsch, et al., *Science,* 227:1229, 1985, both incorporated herein by reference.

One of skill in the art will be able to select an appropriate vector for introducing the nucleic acid sequences of the invention in a relatively intact state. Thus, any vector which will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

For example, a heterologous nucleic acid sequence can be introduced into a plant cell utilizing *Agrobacterium tumefaciens* containing the Ti plasmid. When using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells (De Framond, *Biotechnology,* 1:262, 1983; Heokema, et al., *Nature,* 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in situ transformation by Agrobacterium, as described by Bechtold, et al., (*C.R. Acad. Sci. Paris,* 316:1194, 1993). This approach is based on the vacuum infiltration of a suspension of Agrobacterium cells.

The preferred method of introducing nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, the enhancer construct described herein can be introduced into a plant cell by contacting the plant cell using mechanical or chemical means. For example, nucleic acid can be mechanically transferred by direct microinjection into plant cells utilizing micropipettes. Moreover, the nucleic acid may be transferred into plant cells using polyethylene glycol which forms a precipitation complex with genetic material that is taken up by the cell.

The nucleic acid can also be introduced into plant cells by electroporation (Fromm, et al., *Proc. Natl. Acad. Sci., U.S.A.,* 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize plant membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., *Nature* 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). The CaMV viral DNA genome is inserted into a parent bacterial plasmid creating a recombinant DNA molecule which can be propagated in bacteria. After cloning, the recombinant plasmid may be re-cloned and further modified by introduction of the desired nucleic acid sequence. The modified viral portion of the recombinant plasmid is then excised from the parent bacterial plasmid, and used to inoculate the plant cells or plants.

In the examples that follow, tobacco plants are transformed generally by the method of Rogers, et al. (*Methods Enzymol.* 118:627, 1986). Briefly, tobacco leaf disks are taken from surface sterilized tobacco leaves and cultivated on Murashige-Skoog (MS) medium to promote partial cell formation at the wound surfaces. The leaf disks are then submerged in a culture of *A. tumefaciens* cells containing a plasmid having the desired combination of enhancer, promoter and gene of interest. The disks are then cultivated on MS medium with kanamycin on which only transformed cells will grow into calli. Shoots then grow and plantlets are regenerated from the callus by growing in rooting medium.

Palindromic element binding factor (PABF)

The present invention also provides a substantially pure palindromic element binding factor (PABF) characterized as having a molecular weight of about 67 kDa as determined by reducing SDS-PAGE, binding to a $(AATT)_n$ repeat element, where $n \geq 2$ (as described in detail above); and having a H1 histone-like domain, a glutamine rich domain and a HMG I/Y-like domain, reading in the N terminal to C-terminal direction.

The term "substantially pure" as used herein refers to PABF which is substantially free of other proteins, lipids, carbohydrates or other materials with which it is naturally associated. One skilled in the art can purify PABF using standard techniques for protein purification. The substantially pure polypeptide will yield a single major band on a non-reducing or reducing polyacrylamide gel. The purity of the PABF polypeptide can also be determined by amino-terminal amino acid sequence analysis. PABF polypeptide includes functional fragments of the polypeptide, as long as the activity of PABF remains intact (i.e., the fragments function as transcription factors and retain the ability to bind to a $(AATT)_n$ repeat element). Such polypeptides include immunologically reactive peptides capable of inducing antibody production. The preferred PABF of the invention is derived from a plant cell.

The invention provides isolated polynucleotides encoding PABF polypeptide. These polynucleotides include DNA, cDNA and RNA sequences which encode PABF. It is understood that all polynucleotides encoding all or a portion of PABF are also included herein, as long as they encode a polypeptide with PABF activity, i.e., the encoded peptide acts as a transcription factor and retains the ability to bind to a $(AATT)_n$ repeat element. Such polynucleotides include naturally occurring, synthetic, and intentionally manipulated polynucleotides. For example, PABF polynucleotide may be subjected to site-directed mutagenesis. The polynucleotide sequence for PABF also includes antisense sequences. The polynucleotides of the invention include sequences that are degenerate as a result of the genetic code. There are 20 natural amino acids, most of which are specified by more than one codon. Therefore, all degenerate nucleotide sequences are included within the present invention.

Specifically disclosed herein is a DNA sequence encoding the tobacco PABF. The sequence contains an open reading frame encoding a polypeptide of about 546 amino acids in length. Preferably, the plant PABF nucleotide sequence of the present invention is the sequence set forth in SEQ ID NO:2 and the amino acid sequence is preferably SEQ ID NO:3 (FIG. 5).

Figures 1, 1A, 2:
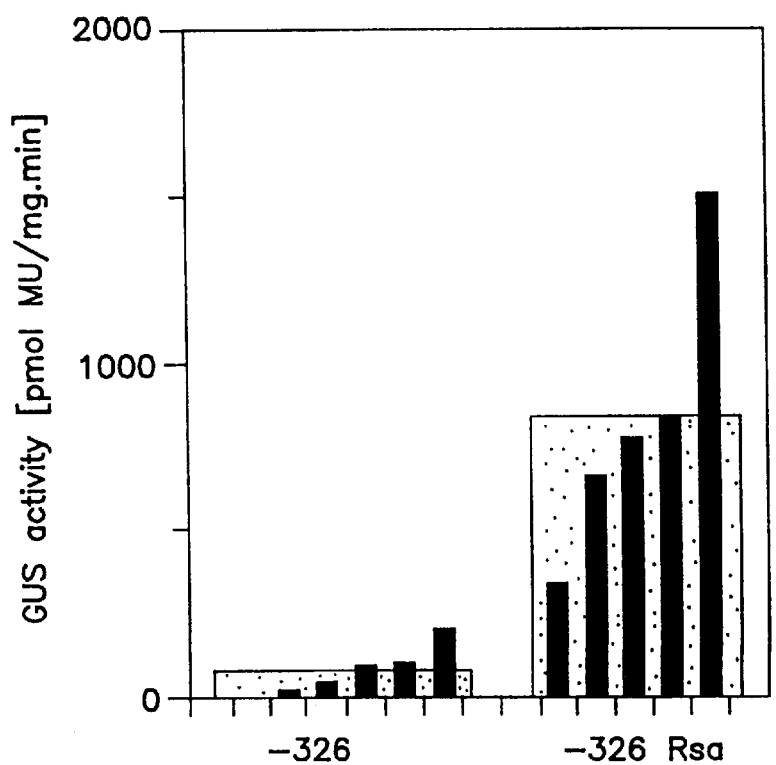
Figures 1, 1A, 2, 3:
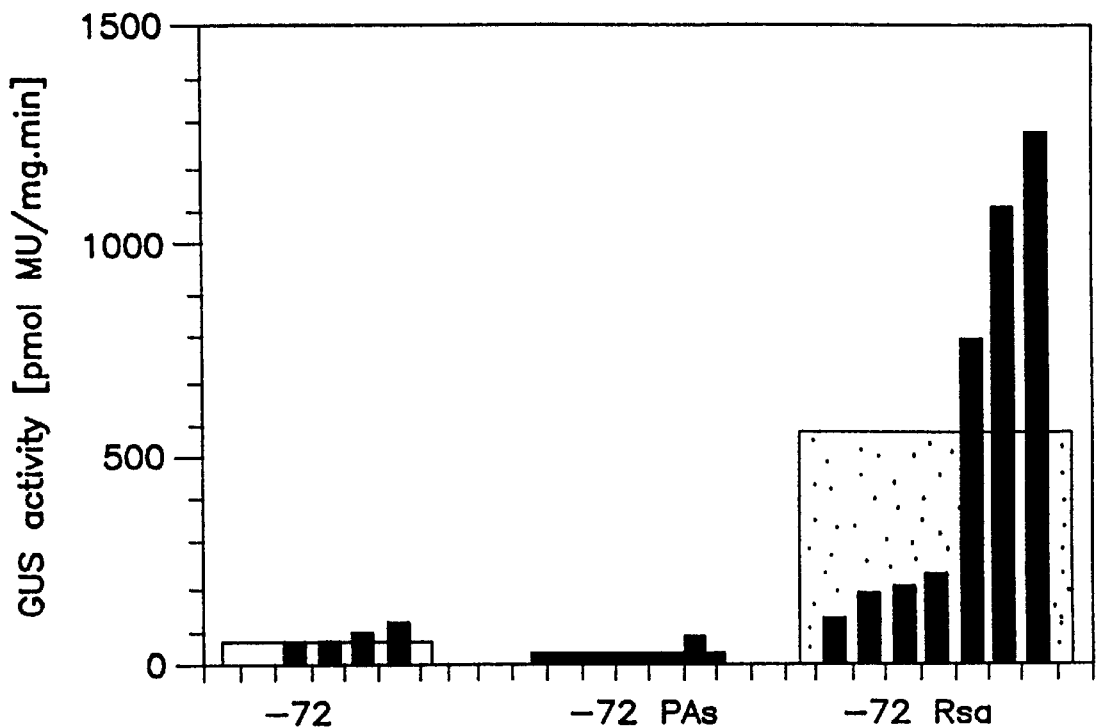
FIG. 3 shows a DNASE I footprint analysis of the RsaI fragment with bean nuclear extract. The end-labeled RsaI fragment was incubated in the presence (+) or absence (−) of bean nuclear extract and subsequently digested with 0.25 and 1 units/ml DNase I, respectively. Digestion products were analyzed on a 6% denaturing polyacrylamide gel together with Maxam-Gilbert A and G sequencing reactions (lane A/G) of the same DNA fragment. The region protected from DNase I digestion is indicated and the corresponding sequence is outlined on the left hand side (SEQ ID NO:9). Numbering indicates nucleotide position relative to the transcription start site.
Figures 1, 1A, 2, 3, 4:
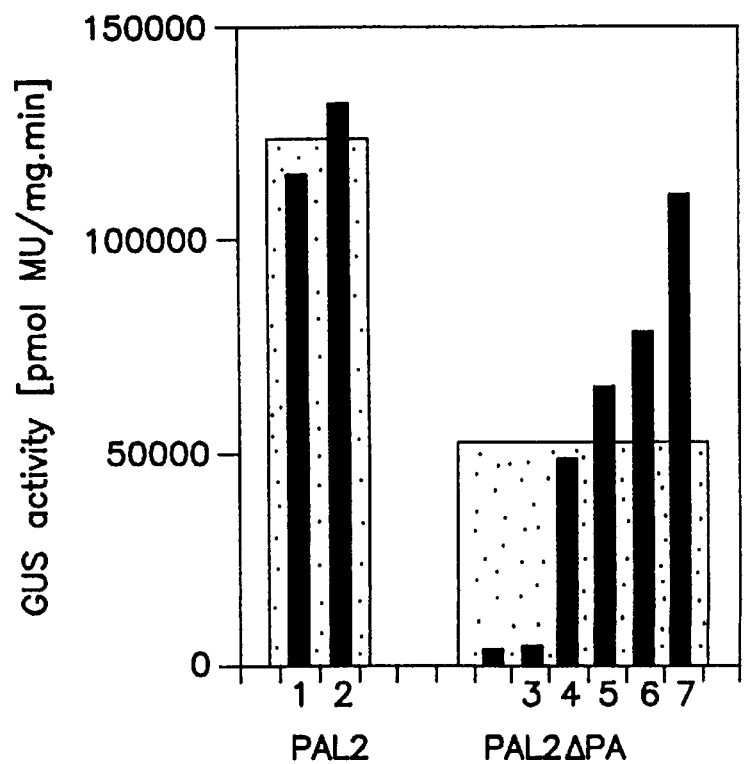
Figures 1, 1A, 2, 3, 4, 5:
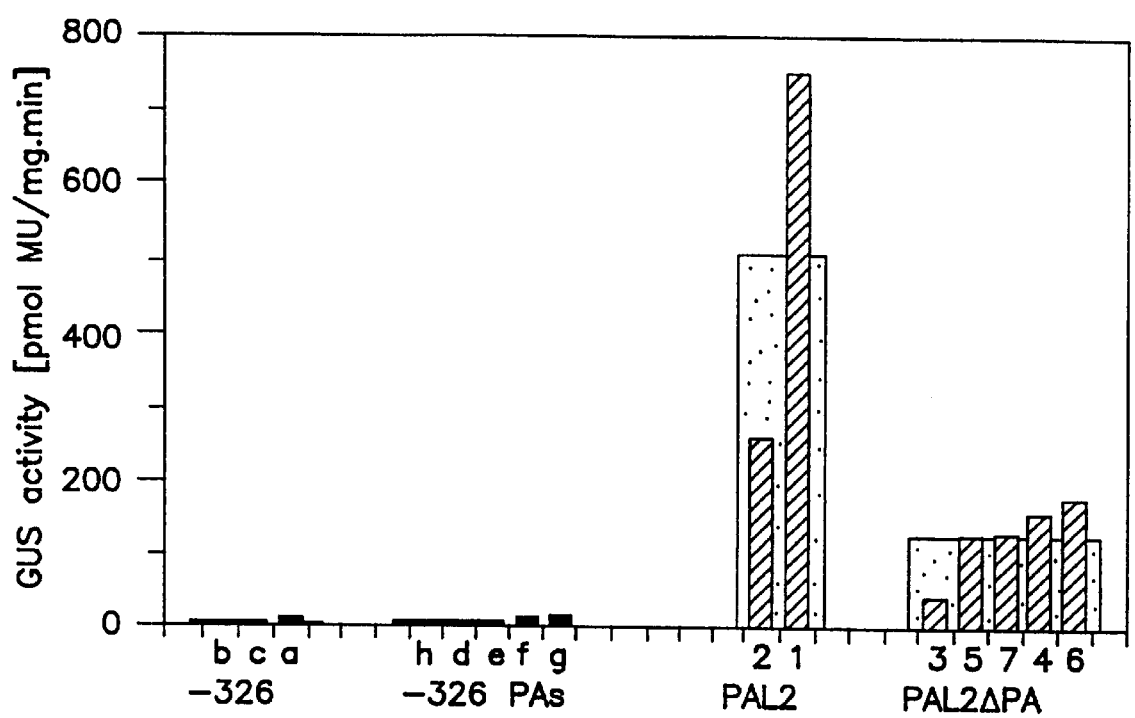

Polynucleotides encoding PABF includes SEQ ID NO:2 as well as nucleic acid sequences complementary to SEQ ID NO:2 (FIG. 5). Complementary sequences may include antisense nucleic acids. When the sequence is RNA, the deoxynucleotides A, G, C, and T of SEQ ID NO:2 are replaced by ribonucleotides A, G, C, and U, respectively. Also included in the invention are fragments of the above-described nucleic acid sequences that are at least 15 bases in length, which length is sufficient to permit the fragment to selectively hybridize to DNA that encodes the protein of SEQ ID NO:3 under physiological conditions. Specifically, the term "selectively hybridize" means that a fragment hybridizes to DNA encoding PABF protein under moderate to highly stringent conditions (see Sambrook, Fritsch and Maniatis, *Molecular Cloning: A Laboratory Manual* (2d ed.)).

The PABF nucleic acid sequence described in the Examples below, contains one long open reading frame of 546 amino acids, assuming that the first ATG is used as the translational start site. This gives rise to a protein with an apparent calculated relative molecular mass ($M_r$) of 67 kDa. Southwestern blot analysis with tobacco nuclear extracts fractioned on an SDS polyacrylamide gel confirmed that PABF polypeptide binds to the $(AATT)_n$ enhancer element (Example 3).

Hydrophobicity prediction analyses (Kyte and Doolittle, *J. Mol. Bio.*, 157:105, 1982) indicate that PABF is highly hydrophilic and suggest that PABF contains three distinct domains. Amino acids 38 to 127 in the N-terminus show a high degree of homology to the central, globular domain of histone H1, a basic, chromosomal protein which binds to the linker DNA between nucleosomes, leading to the formation of a higher order structure. The central part of PABF, between amino acids 153 and 231, consists of a glutamine-rich domain. Thirty nine out of 78 amino acids (50%) were glutamine residues and these were uniformly distributed. The C-terminal domain, amino acids 274 to 484, showed a high degree of similarity to mammalian HMG I/Y proteins. HMG I/Y proteins are small basic, non-histone, chromosomal proteins, which preferentially bind AT-rich sequences (Bustin, et al., supra). Binding is mediated by the AT-hook motif, a peptide of 11 amino acids, which is repeated three times in the HMG I/Y gene. Six AT-hook motifs are present in PABF. In addition one N-terminal and one C-terminal half of a seventh. AT hook motif, separated by 7 amino acids, is found. The originally isolated C-terminal part of PABF domain contains 3 AT-hook motifs, strongly suggesting that this motif is responsible for PABF's DNA-binding activity.

Minor modifications of the PABF primary amino acid sequence may result in proteins which have substantially equivalent activity as compared to the PABF polypeptide described herein. Such proteins include those as defined by the term "having substantially the amino acid sequence of SEQ ID NO:3". Such modifications may be deliberate, as by site-directed mutagenesis, or may be spontaneous. All of the polypeptides produced by these modifications are included herein as long as the biological activity of PABF remains. Further, deletion of one or more amino acids can also result in a modification of the structure of the resultant molecule without significantly altering its biological activity. This can lead to the development of a smaller active molecule with potentially broader utility. For example, one can remove amino or carboxy terminal amino acids which are not required for PABF biological activity.

The PABF polypeptide of the invention includes the disclosed sequence (SEQ ID NO:3; FIG. 5) and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Nucleic acid sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the PABF polynucleotide of the invention is derived from a plant. Screening procedures which rely on nucleic acid hybridization make it possible to isolate any gene sequence from any organism, provided the appropriate probe is available. Oligonucleotide probes, which correspond to a part of the sequence encoding the protein of interest, can be synthesized chemically. This requires that short, oligopeptide stretches of amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981; Maniatis, et al., *Molecular Cloning: A Laboratory Manual*, Cold Spring Harbor, N.Y. 1989).

The development of specific DNA sequences encoding PABF can also be obtained by: 1) isolation of double-stranded DNA sequences from the genomic DNA; 2) chemical manufacture of a DNA sequence to provide the necessary codons for the polypeptide of interest; 3) in vitro synthesis of a double-stranded DNA sequence by reverse transcription of mRNA isolated from a eukaryotic donor cell; and PCR of genomic DNA or cDNA using primers capable of annealing to the DNA sequence of interest. In the latter case, a double-stranded DNA complement of mRNA is eventually formed which is generally referred to as cDNA.

The synthesis of DNA sequences is frequently the method of choice when the entire sequence of amino acid residues of the desired polypeptide product is known. Among the standard procedures for isolating cDNA sequences of interest is the formation of plasmid- or phage-carrying cDNA libraries which are derived from reverse transcription of mRNA which is abundant in donor cells that have a high level of gene expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for PABF peptides having at least one epitope, using antibodies specific for PABF. Such antibodies can be either polyclonally or monoclonally derived and used to detect expression product indicative of the presence of PABF cDNA.

DNA sequences encoding PABF can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

Parts obtained from the regenerated plant, such as flowers, seeds, leaves, branches, fruit and the like are within the claimed invention, provided that these parts comprise cells which have been transformed according to the present invention. Progeny and variants and mutants of the regenerated plants are also included in the scope of the invention provided that these parts comprise the introduced nucleic acid sequences of the invention.

In the present invention, the PABF polynucleotide sequences may be inserted into a recombinant expression vector. The term "recombinant expression vector" refers to a plasmid, virus or other vehicle known in the art that has been manipulated by insertion or incorporation of the PABF genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells.

Polynucleotide sequences encoding PABF can be expressed in plants, prokaryotes or eukaryotes. Hosts can include plant cells as well as microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art.

Isolation and purification of recombinantly expressed polypeptide, or fragments thereof, provided by the invention, may be carried out by conventional means including preparative chromatography and immunological separations involving monoclonal or polyclonal antibodies.

The PABF polypeptides of the invention can also be used to produce antibodies which are immunoreactive or bind to epitopes of the PABF polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference).

Antibodies which bond to the PABF polypeptide of the invention can be prepared using an intact polypeptide or fragments containing small peptides of interest as the immunizing antigen. For example, it may be desirable to produce antibodies that specifically bind to the N- or C-terminal domains of PABF. The polypeptide or a peptide used to immunize can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

It is also possible to use the anti-idiotype technology to produce monoclonal antibodies which mimic an epitope.

The method of increasing gene expression as described herein comprises operably linking an (AATT)$_n$ repeat element to a heterologous promoter in operable linkage with the gene to be expressed, and optionally contacting the repeat element with PABF polypeptide to further boost gene expression. As discussed earlier, PABF is a DNA binding protein that binds to the (AATT)$_n$ repeat element, as shown in the Examples below, and further "boosts" the activity of the (AATT)$_n$ enhancer element. For an additional boost, it may be desirable to operably link a PABF encoding polynucleotide to the promoter region operably linked to the (AATT)$_n$ repeat element. While not wanting to be bound by a particular theory, it is believed that enhanced expression of PABF in operable linkage to both a promoter and the (AATT)$_n$ repeat element of the invention will form a positive feedback loop, whereby PABF induces expression of itself by binding to the (AATT)$_n$ repeat element and stimulating continuous enhancement of its own expression.

The above disclosure generally describes the present invention. A more complete understanding can be obtained by reference to the following specific examples which are provided herein for purposes of illustration only and are not intended to limit the scope of the invention.

EXAMPLES

The following examples describe the identification of an (AATT)-repeat PA cis-element within the upstream region of the PAL2 promoter, which functions as a non-specific enhancer. General enhancement of specific transcription patterns was observed when this motif was operably linked to a heterologous promoter. A novel factor was cloned which binds to this element through AT-hook DNA-binding modules present in its C-terminal domain. This factor has a novel tripartite domain structure, the aggregate functional attributes of which match the activity of the cognate cis-element as a non-specific enhancer.

EXAMPLE 1

Materials and Methods

Plasmid construction and plant transformation—The 153 bp RsaI fragment of the PAL2 promoter (Cramer, et al., *Plant Mol. Biol.*, 12:367, 1989) was cloned into the filled-in HindIII site upstream of the -326 and -72 CHS15 promoter/GUS gene fusion (Stermer, et al., *Mol. Plant-Microb. Int.*, 3:381, 1990). Similarly, (AATT)$_3$ oligonucleotides were synthesized, kinased, ligated and after a fill-in reaction cloned into the SmaI site of pGEM 7. One plasmid (pPAs) contained an insert of the sequence (AATT)$_{13}$, which was designated PAs for synthetic pallindromic (PA) element. This fragment was used to subclone the PAs motif upstream of the -326 and -72 CHS15 promoter/GUS gene fusions. Transgenic tobacco plants were generated by leaf disc transformation using *Agrobacterium tumefaciens* LB4404 (Rogers, et al., *Methods Enzymol.*, 118:627, 1986) and grown on MS medium (Murashige and Skoog, *Physiol. Plant*, 15:473, 1962) with 200 ug/ml kanamycin under a 16 h light /8 h dark cycle at 25° C.

Fluorometric GUS assay—GUS activity in tissue extracts was determined by measuring the production of 4-methylumbelliferone (MU) from the corresponding glucuronide (Jefferson, et al., *EMBO J.*, 6:3901, 1987) with a Fluoro/Colorimeter (American Instrument Company). Protein concentration was determined according to Bradford (Bradford, M. M., *Anal. Biochem.*, 72:248, 1976).

General molecular biological techniques—Tobacco DNA was isolated from leaves (Murray and Thompson, *Nucl. Acids Res.*, 8:4321, 1980) and total RNA was prepared from various tobacco tissues (Chirgwin, et al., *Biochemistry*, 18:5294, 1979). For Southern and Northern blots, nucleic acids were transferred onto Nytran membranes (Schleicher and Schüll). Hybridization was carried out at 60° C. (Church and Gilbert, *Proc. Natl. Acad. Sci. USA*, 81:1991, 1984) and membranes were washed twice in 2× SSC, 1% SDS at room temperature, once in 0.2×SSC, 1% SDS at 60° C., and for lower stringency hybridization in 1× SSC, 1% SDS at 60° C. Probes were prepared by random priming (Feinberg and Vogelstein, *Anal. Biochem.*, 132:6, 1983) of the λ900 cDNA fragment. Oligonucleotides were synthesized on a Millipore (Bedford, Mass.) DNA synthesizer.

Sequences of the different oligonucleotides used as probes were (5'-3'):
PA: (AATTAATTAATCAATTAATTAATTAATTGATTGATT)(SEQ ID NO:1));
PF: (CATAAGGATTAGGAATTTAATTTCGTAG)(SEQ ID NO:4));
AT: (TATATATATATATATATATATATATATATATACCACGT (SEQ ID NO:5));
AC: (CTTGTCATTATTTCTCCACCAACCCCCTTCACTT CCC(SEQ ID NO:6);
G-box: (TGCAGGTGTTGCACGTGATACTCACCTACCCT GCA(SEQ ID NO:7));
H-box: (CGACTCACCTACCTGACATGCTACGCAGCG (SEQ ID NO:8)).

The cDNA encoding PABF was sequenced on both strands (Sanger, et al., *Proc. Natl. Acad. Sci. USA*, 74:54563, 1977) after generation of a series of nested deletions. Sequence data were analyzed using the University of Wisconsin genetics computer group sequence analysis software package (Devereux, et al., *Nucl. Acids Res.*, 12:387, 1984) and homology searches were performed with the Blast network service (Altshul, et al., *J. Mol. Biol.*, 215:403, 1990).

Electrophoretic mobility shift assay (EMSA)—Binding reactions were carried out in 20 ml containing 2×10$^4$ cpm of the $^{32}$P labeled probe, 20 µg of nuclear extract (Staiger, et al., *Proc. Natl. Acad. Sci. USA*, 86:6930, 1989) from cultured bean cells (cultivar Canadian Wonder) and tobacco stems, respectively, 6 µg of poly[dI-dC] in the following binder buffer: 20 mM Hepes, pH 7.9/20% glycerol/0.2 M KCl/0.4 mM EDTA/0.5 mM PMSF/2 mM MgCl$_2$/1 mM DTT (Ausubel, et al., *Current Protocols in Molecular Biology*, John Wiley & Sons, NY, 1992). Complementary oligonucleotides with the PA motif (AATTAATTAATCAATTAATTAATTAATTGATTGATT) (SEQ ID NO:1) were kinased, annealed and ligated to generate concatermerized PA elements (Vinson, et al., *Genes Dev.*, 2:801, 1988). The gel purified pentamer was used as a probe. Restriction fragments were labeled by a fill-in reaction with Klenow polymerase.

DNase I footprint analysis—DNase I foot printing was performed according to Ausubel et al. (Ausubel, et al., supra). Briefly, the noncoding strand of the 153 bp RsaI PAL2 promoter fragment (-410 to -255) subcloned into pGEM7 was labeled by filling in a recessed 3'-end of a BamHI site present in the multiple cloning site of the vector. The labeled fragment was incubated with 10 µg bean nuclear extract in a 50 ml reaction for 10 min at 0° C. and 20 min at 25° C. prior to DNase I digestin for one min at 25° C. with 0.25 and 1 u/ml, respectively. An aliquot of the labeled fragment was used for sequencing with the chemical degradation method (Maxam, et al., *Methods Enzymol*, 65:499, 1980).

Southwestern analysis—A λgt11 library, prepared from tobacco stem RNA, was screened with a probe containing multiple copies of the PA element, generated by concatemerizing a double-stranded PA oligonucleotide. Following growth of recombinant phages and isopropyl β-thiogalactoside induction, proteins were transferred onto nitrocellulose membranes (Schleicher and Schüll). Membrane bound proteins were denatured and renatured (Vinson, et al., supra; Singh, et al., Bio Techniques, 7:252, 1989). After blocking the membranes for 30 min in binding buffer (BB, 20 mM Hepes, pH 7.9/3 mM $MgCl_2$/40 mM KCL/1 mM DTT) supplemented with 5% nonfat dry milk, the filters were hybridized in BB with 0.25% mil, $10^6$ cpm/ml probe and 5 µg/ml denatured salmon sperm DNA for 3 h at room temperature. Filters were washed three times for 10 min with BB prior to autoradiography.

PABF recombinant lysogens were generated in *Escherichia coli* Y1089. Lysogenic extracts (Sambrook, et al., *Molecular Cloning: A Laboratory Manual*, Cold Spring Lab. Press, Second Edition) were separated on a 10% SDS-polyacrylamide gel and transferred to nitrocellulose. After renaturation and blocking with BB with 5% milk at 4° C,. for 9 h, the membrane was cut into strips and hybridized with different probes for 10 h at 4° C. Concatemerized oligonucleotide probes were used without further gel purification. To label PCR fragments $\alpha$-$^{35}$S dCTP was used instead of unlabeled dCTP.

EXAMPLE 2

PA element as a general enhancer—Analysis of 5' deletions of the PAL2 promoter in transgenic tobacco revealed that major quantitative elements are present between positions -480 and -289 relative to the transcription start site (Leyva, et al., *Plant Cell*, 4:263, 1992). FIG. 1, panel B shows the promoter GUS-fusion constructs (not drawn to scale). The 153 bp RsaI fragment of the PAL2 promotor or PAs with an $(AATT)_{13}$ sequence were cloned in front of the -326 CHS15/GUS gene fusion (constructs -326 Rsa and -326 PAs, respectively) or -72 CHS15/GUS gene fusion (constructs -72 Rsa and -72 PAs, respectively). The CHS15 promoter is represented by hatched boxes. The position of the RsaI fragment within the PAL2 promoter (PAL2, dotted) as well as the position of the PA deletion (broken lines) in the PAL2ΔPA construct are indicated. The arrows mark transcription start sites of the reporter gene.

Two striking sequence motifs are present within this region: 19 tandem repeats of the dinucleotide AT (AT-element: -467 to -429) and a palindromic element (PA: -340 to -300), which is an imperfect 10-fold repeat of the sequence AATT. The function of the PA cis-element (-340 to -300) was evaluated by analysis of the effects of placing this sequence upstream of the bean chalcone synthase CHS15 promoter, and by deleting the element from the full length bean PAL2 promoter. Both the 153 bp RsaI fragment of the bean PAL2 promoter from -410 to -255, or a synthetic PA element (PAs) consisting of a perfect $(AATT)_{13}$ sequence were inserted upstream of -326 CHS15/GUS and -72 CHS15/GUS promoter gene fusions (FIG. 1, panel B). The CHS15 promoter, 5' deleted to -326 relative to the transcriptional start site is expressed in pigmented epidermal cells of the petal but not in non-pigmented regions of the petal or in vascular tissues. Further 5' deletion of the CHS15 promoter to -72 abrogates GUS expression in transgenic tobacco and suspension cultured soybean cells (Dron, et al., *Proc. Natl. Acad. Sci. USA*, 85:6738, 1988) by destruction of a G-box 9 (-74 to -68) that is essential for CHS expression.

GUS activity was measured in the pigmented part of the petals from $T_2$ plants transformed with the CHS15/GUS and PAL2/GUS gene fusion constructs summarized in FIG. 1, panel B. Replicate plants of 5 independent -326 transgenic lines and 7 independent -326 PAs lines, respectively, were assayed for extractable GUS activity. FIG. 1A shows a bar graph for GUS activity (mean of two plants for each transgenic line) in extracts of mature pigmented corolla (petal) tissue (panel a–d), unpigmented corolla tissue (panel f) and petioles above the fifth internode (panel e) from independent transformants containing the constructs illustrated in FIG. 1, panel B. The shaded boxes represent the mean values of the GUS activities measured in independent transgenic lines. Letters in panel a and numbers in panel d indicate the transgenic lines from which the GUS data in panels e and f were derived.

GUS activity in pigmented petal tissue of -326 plants is about 100 pmol 4-methylumbelliferone mg protein/min. The presence of the PAs element in -326 PAs plants resulted in up to a 10-fold increase in extractable GUS activity specifically in the pigmented tissue. Five independent transgenic lines transformed with the -326 Rsa construct showed up to an 8-fold increase in GUS activity in the pigmented tissue compared to -326 plants (FIG. 1A, panel b). Increased GUS activity was not seen in other tissues where the wild-type -326 CHS15 promoter was not active. GUS activity for both constructs (-326 PAs, -326 Rsa) was not above background in the unpigmented part of the petal or in petioles (FIG. 1A, panels e and f), suggesting that the observed effect was strictly quantitative.

The result with the -72 minimal CHS15 promoter constructs was different. Analysis of seven independent -72 Rsa lines revealed that this promoter, which no longer showed GUS activity in petals, could still be activated by introduction of the 153 bp RsaI fragment (FIG. 1A, panel c). However, the PAs element alone (9 independent lines) was unable to stimulate GUS expression when placed upstream of the CHS15 promoter deleted to -72 (see -72 PAs in FIG. 1A, panel c). This indicated that although the PAs element had non-specific enhancer activity, it was not able to activate the promoter by itself. The 153 bp RsaI PAL2 fragment presumably contained specific cis-elements in addition to the $(AATT)_n$ element, consistent with previous analysis in the context of the PAL2 promotor (Leyva, et al., supra).

An enhancer function for the PA element was also indicated by experiments in which this element was specifically deleted from the PAL2 promoter (PAL2ΔPA). Thus, GUS activity in the petal and petioles of transgenic plants containing the PAL2ΔPA/GUS gene fusion was substantially lower than in equivalent plants containing a gene fusion with GUS under the control of the wild-type PAL2 promoter (FIG. 1A, panels d and e).

Nuclear extracts contain a heat-stable DNA binding activity for the PA-element—Nuclear factors that bind to the -480 to -289 region of the PAL2 promoter were identified by electrophoretic mobility shift assays (EMSA). FIG. 2, panel A shows electrophoretic mobility shift assays (EMSA) with crude nuclear extracts (NE) of bean (20 mg protein) incubated for 10 min at the indicated temperatures before the labeled RsaI fragment was added. The binding reaction was performed for 30 min at either 0° C. or 25° C.

Two complexes, C1 and 2, were observed when the EMSA binding reaction was performed at room temperature. The major complex, C2, binds about 90% of the probe. To test whether high mobility group proteins (HMG), a class of small chromosomal proteins which preferentially bind AT-rich sequences (Bustin, et al., *Biochem. Biophys. Acta*, 1049:231, 1990), were involved in these complexes, we examined the thermal stability of the binding factors, both complexes were heat stable. Approximately 40% of the originally binding activity in C2 remained after 10 min incubation at 70° C., but was lost after incubation at 80° C. In contrast, complex C1 was stable up to 80° C. and was preferentially formed at higher temperatures.

The expression pattern of the bean PAL2 promoter in transgenic tobacco is very similar to that in bean suggesting conservation of regulatory mechanisms (Liang, et al., *Proc. Natl. Acad. Sci. USA*, 86:9284, 1986b). To test whether similar DNA-binding activities are present in tobacco extracts we performed EMSA with the PA binding site as a probe. A similar, heat stable DNA-binding activity (C2, FIG. 2b) was detected in nuclear extracts prepared from tobacco stems. Only a minor reduction of binding was observed after incubation for 10 min at 80° C. Furthermore, a smaller complex (C1) appeared after heat treatment of the tobacco extract.

FIG. 2, panel B shows electrophoretic mobility shift assays (EMSA) with nuclear extracts (20 mg) prepared from tobacco stems was incubated for 10 min at 80° C. prior to the binding reaction for which a pentamer of the concatemerized PA oligonucleotide was used as probe. Protein-DNA complexes were separated from unbound DNA by electrophoresis (10 V/cm) on 4% nondenaturing polyacrylamide gels with a high ionic strength Tris-glycine buffer. P: free probe, C1 and C2: complexes.

Figures 2A, 2B:
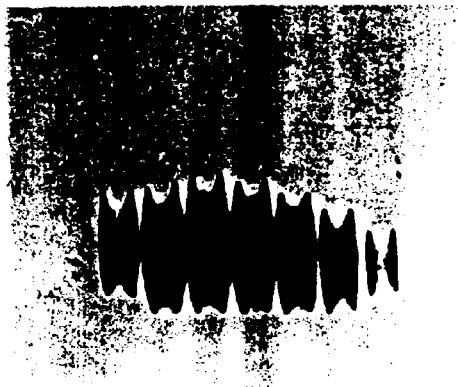
FIG. 2A shows electrophoretic mobility shift assays (EMSA) with crude nuclear extracts (NE) of bean (20 mg protein) incubated for 10 min at the indicated temperatures before the labeled RsaI fragment was added. The binding reaction was performed for 30 min at either 0° C. or 25° C.
FIG. 2B shows electrophoretic mobility shift assays (EMSA) with nuclear extracts (20 mg) prepared from tobacco stems incubated for 10 min at 80° C. prior to the binding reaction for which a pentamer of the concatemerized oligonucleotide (i.e., $(AATT)_5$) was used as probe. Protein-DNA complexes were separated from unbound DNA by electrophoresis (10 V/cm) on 4% nondenaturing polyacrylamide gels with a high ionic strength Tris-glycine buffer. P: free probe, C1 and C2: complexes.
Figure 3:
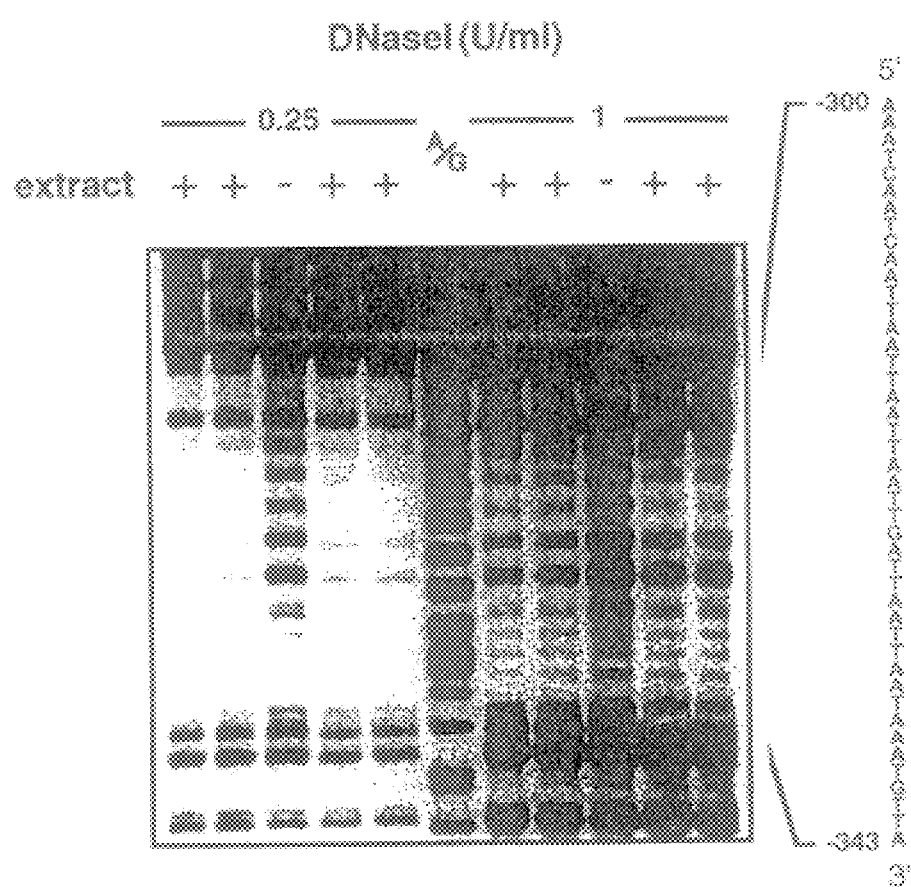

A DNA-binding activity present in bean nuclear extracts was identified which showed specificity for the 153 bp RsaI restriction fragment (-410 to -255) covering most of this region (FIG. 2A).

The end-labeled RsaI fragment was incubated in the presence of (+) or absence (−) of bean nuclear extract and subsequently digested with 0.25 and 1 units/ml DNase I, respectively. Digestion products were analyzed on a 6% denaturing polyacrylamide gel together with Maxam-Gilbert A and G sequencing reactions (lane A/G) of the same DNA fragment. The region protected from DNase I digestion is indicated and the corresponding sequence is outlined on the left hand side. Numbering indicates nucleotide position relative to the transcription start site a of the PAL2 promoter. DNase I footprint analysis of trans-factor binding to the 153 bp RsaI fragment revealed a single protected site (-343 to -300), which mapped exactly to the (AATT)-repeat PA element (FIG. 3).

EXAMPLE 3

A tobacco cDNA encoding a PA-specific DNA-binding protein—To identify proteins that interact with PA element, a λgt11 expression library prepared from tobacco (*Nicotiana tabacum*) stem RNA was screened for DNA binding proteins with a PA probe. A singe recombinant phage (λ900) expressing a DNA-binding protein (PABF) that bound the PA probe was isolated after screening of $1 \times 10^6$ plaques.

To determine whether the binding of PABF was specific for the PA probe or had a general DNA binding activity, DNA-protein filter binding assays were performed. After induction with IPTG, proteins from λ900 plaques were transferred to nitrocellulose which was cut into 9 segments and hybridized with different probes. PA, which was used for the screening, was strongly bound by PABF. Binding of PAs, which was used for the functional studies in transgenic plants, was indistinguishable from PA binding. An AT-rich region (AT), consisting of a 19-fold repeat of AT, is present upstream of the PA element of PAL2 within the -480 to -289 region. Despite the similarity to PA, no binding was observed with the AT probe. An additional uninterrupted stretch of 10 AT base pairs $(AATTT)_2$, designated PF, is located between the AT and PA motifs of the PAL2 promoter, but this element was likewise not bound by PABF. In addition we tested probes not particularly rich in AT base pairs: the AC-rich element of the PAL-2 promoter as well as various mutated versions (mAC-1, -2, -3), the G-box (Giuliano, et al., *Proc. Natl. Acad. Sci. USA*, 85:7089, 1988) and H-box (Loake, et al., *Proc. Natl. Acad. Sci. USA*, 89,9230, 1992) motifs. None of these motifs was bound by PABF.

Figure 4A:
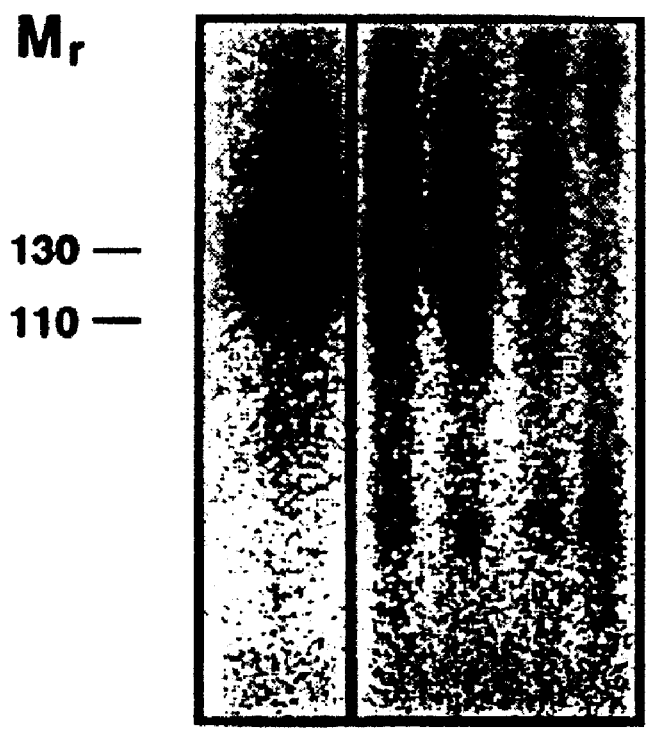
FIGS. 4A–4B show Southwestern blot analyses of protein extracts from cultures lysogenic for λ900 probed with multimerized PA probes. Panel A is protein extracts of the lysogenic phage separated on SDS-PAGE, blotted onto nitrocellulose and renatured. The membrane was cut into 6 strips and hybridized with the indicated probe. M: position of marker proteins with an apparent molecular mass given in kDa; $PA_n$; concatermerized PA probe; PA: monomeric PA probe; 1–4: PCR-products representing different regions of the PAL2 promoter. Panel B shows the relative positions of PCR products 1–4 within the PAL2 promoter. Position of the phloem-element, AT-, PF- and PA-motifs are indicated. Numbers refer to the position relative to the transcription start site. The arrow indicates the 130 kDa phage-encoded fusion protein.
Figure 4B:
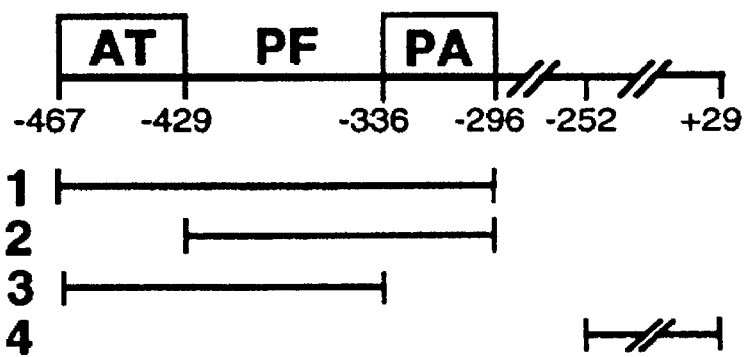
Figure 6:
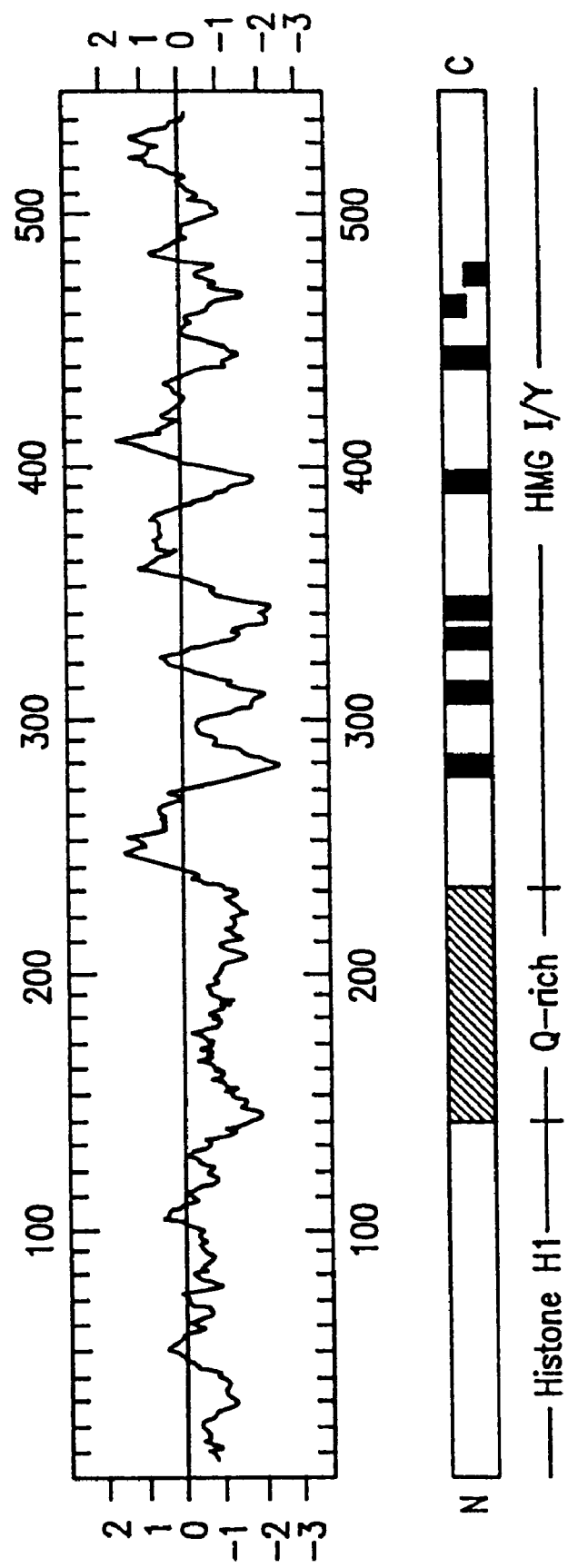

FIG. 4 shows Southwestern blot analyses of protein extracts from cultures lysogenic for λ900 probed with multimerized PA probes. FIG. 4, panel A is protein extracts of the lysogenic phage separated on SDS-PAGE, blotted onto nitrocellulose and renatured. The membrane was cut into 6 strips and hybridized with the indicated probe. M: position of marker proteins with the actual molecular mass given in kDa; $PA_n$: concatemerized PA probe; PA: monomeric PA probe; 1–4: PCR-fragments representing different regions of the PAL-2 promoter. FIG. 4B shows the relative position of PCR fragments 1–4 within the PAL2 promoter. Position of the phloem-element, AT-, PF- and PA-motifs are indicated. Numbers refer to the position relative to the transcription start site. The arrow indicates the 130 kDa phage-encoded fusion protein.

Southwestern blot analysis of protein extracts from cultures lysogenic for λ900 probed with the multimerized PA probe ($PA_n$) detected a fusion protein of about 130 kDa (FIG. 4, panel A). Compared with binding to $PA_n$, the monomeric PA element was bound only weakly, and most of the probe was bound by a bacterial protein of about 33 kDa (FIG. 4, panel A, lane PA). However, in the context of the PAL2 promoter, PABF recognizes a single PA element. Thus, fragments of the 200 bp PAL 2 promoter region -480 to -280 were generated by PCR using a full promoter construct (PAL2) or constructs in which either the PA element (PAL2ΔPA) at the AT-stretch (PAL2ΔAT) were deleted (FIG. 4, panel B). A fragment from outside this region was included as a control. Only fragments with an intact PA element were bound by the DNA-binding protein (FIG. 4, panel A, lanes 1 and 2). Thus, PABF bound not only to the multimerized PA probe but also strongly bound the PA element embedded within the PAL2 promoter.

Transcript size and expression pattern of PABF—The size of the PABF transcript was determined by northern blot analysis to be about 2.2 kg. Analysis of total RNA prepared from root, stem, leaf, and flower, tissue of tobacco for PABF mRNA levels revealed strong expression of PABF in all tissues when compared to the β-ATPase gene, known to be constitutively expressed (Boutry and Chua, *EMBO J.*, 4:2159, 1985). Slightly higher steady state PABF mRNA levels were detected in stem and leaf tissues than in other tissues.

PABF is an HMB I/Y-like protein with a tripartite structure—The northern blot data indicated that λ900, which contained a 850 bp cDNA fragment with a poly(A) tail, was not full length cDNA clone. To isolate a full length cDNA this 3'-fragment was used to screen a λgt11 flower bud library. $4 \times 10^5$ plaques were screened and the largest clone isolated (λ2200) contained a 2153 bp fragment which was sequenced on both strands (FIG. 5).

The sequence of λ900 was identical to the 3'-sequence of λ2200 (FIG. 5, nucleotides 1182–1992) except for a missing poly(A) tail. λ2200 contains one long open reading frame of 546 amino acids, assuming that the first ATG is used as the translational start site. This gives rise to a protein with a calculated relative molecular mass ($M_r$) of 67 kDa. FIG. 5 shows the nucleotide and deduced amino acid sequence of the PABF cDNA (SEQ ID NO:2 and 3, respectively). The deduced amino acid sequence, shown in the one-letter code, starts with the first methione of the open reading frame at position 61 and terminates at the stop codon following N-546. The arrows indicate the 5' and 3'-end of the originally isolated truncated cDNA clone. The AT-hook motifs are underlined. Southwestern blot analysis with tobacco nuclear extracts fractioned on an SDS polyacrylamide gel confirmed that besides small proteins of about 18 kDa, which are presumably HMG proteins and histones, other HMG-like proteins in the range of 40 kDa to 80 kDa, including PABF, were able to bind the PA probe.

Figures 1, 1A, 2, 3, 4, 5, 6:
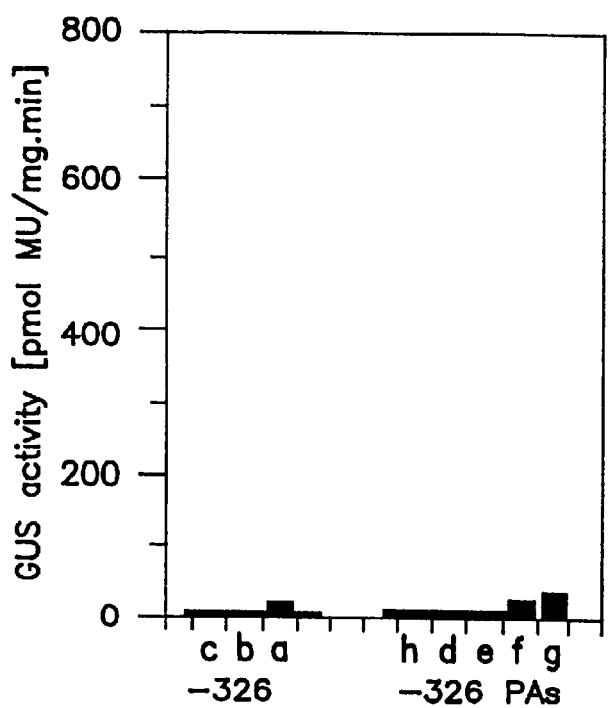
FIG. 6 is a hydrophobicity plot. The top panel shows the hydrophobicity plot with negative values representing hydrophillic areas. The numbering refers to the amino acid position within the PABF sequence. The bottom panel schematically shows the organization of PABF. The black boxes indicate AT-hook motifs found in the HMG I/Y domain.
Figure 1B:
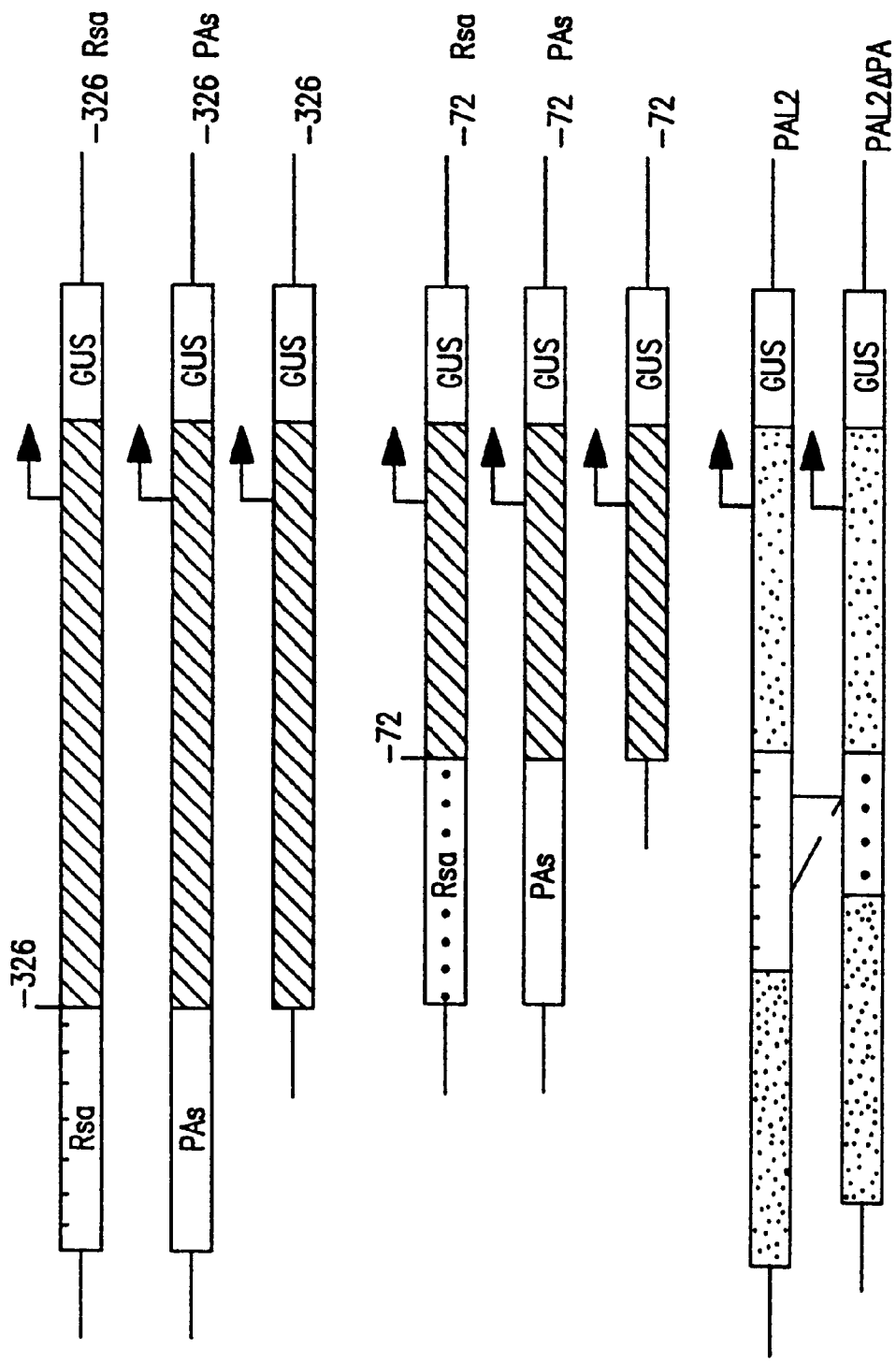
FIG. 1B is an illustration of promoter GUS-fushion constructs (not drawn to scale). The 153 bp RsaI fragment of the PAL2 promoter or synthetic pallindromic sequences (PAs) with an $(AATT)_{13}$ sequence were cloned in front of the −326 CHS15/GUS gene fushion (constructs −326 Rsa and −326 PAs, respectively) or −72 CHS15/GUS gene fushion (constructs −72 Rsa and −72 PAs, respectively). The CHS15 promoter is represented by hatched boxes. The position of the RsaI fragment within the PAL2 promoter (PAL2, dotted) as well as the position of the PA deletion (broken lines) in the PAL2ΔPA construct are indicated. The arrows mark transcription start sites; GUS indicates the reporter gene.

FIG. 6 is a hydrophobicity plot. The top panel shows the hydrophobicity plot with negative values representing hydrophilic areas. The numbering refers to the amino acid position within the PABF sequence. The bottom panel schematically shows the organization of PABF. The black boxes indicate AT-hook motifs found in the HMG I/Y domain. Hydrophobicity prediction (Kyte and Doolittle, *J. Mol. Bio.*, 157:105, 1982) indicated that PABF was highly hydrophilic and suggested that PABF might contain three distinct domains (FIG. 6, top panel). This structural organization was confirmed by data base searches for similarity to the deducted amino acid sequence of PABF (FIG. 6). Amino acids 38 to 127 in the N-terminus showed a high degree of similarity to the central, globular domain of histone H1, a basic, chromosomal protein which binds to the liner DNA between nucleosomes, leading to the formation of a higher order structure (FIG. 7A). The central; part of PABF, between amino acids 153 and 231, consisted of a glutamine-rich domain. Thirty nine out of 78 amino acids (50%) were glutamine residues and these were uniformly distributed. The C-terminal domain, amino acids 274 to 484, showed a high degree of similarity to mammalian HMG I/Y proteins. HMG I/Y proteins are small basic, non-histone, chromosomal proteins, which preferentially bind AT-rich sequences (Bustin, et al., supra). Binding is mediated by the AT-hook, a peptide motif of 11 amino acids, which is repeated three times in HMG I/Y. Six short sequences repeats resembling this AT-hook motif were present in PABF (FIGS. 6 and 7B). In addition one N-terminal and one C-terminal half of this DNA-binding module, separated by 7 amino acids, were found. The originally isolated C-terminal part of PABF contained 3 of these binding modules, which strongly suggested that this motif was responsible for is DNA-binding activity.

Genomic organization of PABF—To determine the organization of PABF genes in the tobacco genome a Southern blot was performed under low stringency conditions. With 5 restriction endonucleases, 2 or 3 hybridizing fragments of equal intensities were observed indicating that PABF was a member of a small gene family of most probably 2 genes. Due to the amphidiploid nature of *N. Tabacum*, these signals may correspond to the PABF genese of two ancestral tobacco species *N. sylvestris* and *N. tomentosiformis*. About half of the cDNAs isolated after rescreening the flow library showed a different restriction pattern compared to the PABF cDNA. Sequence analysis indicated that the second gene was about 94% identical to PABF, with the AT-hook motifs especially well conserved.

SUMMARY

PA functions as a non-specific enhancer—The above Examples show that the synthetic PA element (PAs) has the function of a quantitative cis-element within the bean PAL2 promoter. Thus, when placed upstream of the bean CHS15 promoter, this element stimulated expression about 10-fold in transgenic tobacco without altering the spacial or temporal pattern of expression directed by the homologous promoter. Several AT-rich elements in plant genes have been shown to enhance transcription from the cauliflower mosaic virus (CaMv) 35S -90 promoter in an orientation independent manner. However, in these cases the upstream elements modify the expression pattern of the promoter (Bustos, et al., *Plant Cell*, 1:839, 1989: Jordano, et al., *Plant Cell*, 1:855, 1989). Two other studies have also implicated AT-rich regions in tissue-specific expression (Jofuku, et al., *Nature*, 328:734, 1987; Jensen, et al., *EMBO J.*, 7:1265, 1988). In contrast, modification of expression pattern was not seen with the PAL2PA element. Thus, introduction of the PA element does not affect the expression pattern of the CHS15 promoter demonstrating that the PAs element acts as a general enhancer.

PABF specifically binds to the PA motif—Bean nuclear proteins formed a very heat-stable complex with a 153 bp RsaI fragment inducing the PA element. Dnase 1 footprint analysis identified the PA element as the binding site for the bean nuclear protein. A high degree of thermal stability and preferential binding of AT-rich sequences are characteristics of HMG proteins, which are small, operationally defined, basic, nonhistone chromosomal proteins (Bustin, et al., supra). In some cases, plant DNA-binding activities specific for AT-rich upstream sequences have been identified as HMG proteins (Czarnecka, et al., supra; Jacobsen et al., *Plant Cell*, 2:85, 1990; Pedersen, et al., *Plant Mol. Biol.*, 16:95, 1991). The data above show two heat-stable complexes with different electrophoretic mobilities, C1 and C2, suggesting the presence of distinct HMG proteins with different affinities for AT-rich sequences. A similar binding pattern was also observed by Czarnecka et al. (Czarncka, et al., supra) and upon fractionation by SDS-PAGE, the low mobility complex separated into 46–69 kDa polypeptides, while the high mobility complex resolved into two proteins of 32 and 23 kDa, respectively (Czarnecka, et al., supra).

PABF Function—The novel combination of a glutamine-rich tract sandwiched between the histone H1 and HMG I/Y chromosomal proteins domains in PABF would provide concerted, non-specific stimulation of transcription. Thus, binding of PABF to the cognate (AATT) repeat cis-element might increase transcription not only by local reorganization of nucleosome structure to alleviate histone H1-mediated basal repression and to facilitate general access of transcription factors to the promoter, but also by positioning the glutamine-rich tract to enhance the formation of transcription initiation complexes. Each component would be expected to be non-specific in action and the combined, possibly synergistic functional attributes of this chimeric protein are consonant with the properties of the cognate (AATT)-repeat cis-element as a non-specific enhancer dependent on the presence of specific cis-elements and inactive in the context of a minimal promoter. Thus interaction of PABF with the PA element in the PAL2 promoter provides a mechanism for enhancing selective expression specified by downstream vascular-specific cis-elements that in isolation give only weak xylem-specific expression. Moreover, PABF may be the prototype of a novel class of transcription factors in which transcriptional activation domains are juxtaposed in various combinations with chromosomal protein domains for non-specific quantitative modulation of promoter strength.

Although the invention has been described with reference to the presently preferred embodiment, it should be understood that various modifications can be made without departing from the spirit of the invention. Accordingly, the invention is limited only by the following claims.

What is claimed is:

1. A substantially purified palindromic element binding factor (PABF) polypeptide, characterized as:
   a) having a molecular weight of approximately 67 kD, as determined by SDS-PAGE;
   b) binding to an (AATT)n repeat element, where n≧2; and
   c) having an H1 histone domain, a glutamine rich domain, and an HMG/Y domain.

2. The polypeptide according to claim 1, wherein the amino acid sequence of said polypeptide is set forth as SEQ ID NO:3 or a conservative variation thereof.

3. A substantially purified palindromic element binding factor (PABF) polypeptide comprising the amino acid sequence as set forth in SEQ ID NO:3.

* * * * *

UNITED STATES PATENT AND TRADEMARK OFFICE
CERTIFICATE OF CORRECTION

PATENT NO.     : 6,191,258 B1
DATED          : February 20, 2001
INVENTOR(S)    : Lamb et al.

It is certified that error appears in the above-identified patent and that said Letters Patent is hereby corrected as shown below:

Column 2,
Lines 27, 31 and 32 cancel "fushion" and replace it with -- fusion --.

Column 12,
Line 53, cancel "bond" and replace it with -- bind --.

Column 14,
Line 43, cancel "binder" and replace it with -- binding --.
Line 63, cancel "digestin" and replace it with -- digestion --.

Column 15,
Line 13, cancel "mil" and replace it with -- milk --.

Column 17,
Line 53, cancel "singe" and replace it with -- single --.

Column 18,
Line 22, cancel "position" and replace it with -- positions --.
Line 65, cancel "1992" and replace it with -- 1993 --.

Column 19,
Line 27, cancel "deducted" and replace it with -- deduced --.
Line 30, cancel "liner" and replace it with -- linker --.
Line 55, cancel "genese" and replace it with -- genes --.
Line 57, cancel "flow" and replace it with -- flower --.

Signed and Sealed this

Seventeenth Day of June, 2003

JAMES E. ROGAN
*Director of the United States Patent and Trademark Office*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO:1:

AATTAATTAA TCAATTAATT AATTAATTGA TTGATT                              36

(2) INFORMATION FOR SEQ ID NO:2:

(i) SEQUENCE CHARACTERISTICS:
       (A) LENGTH: 2165 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 61..1698

(xi) SEQUENCE DESCRIPTION: SEQ ID NO:2:

```
CTGAATTTCA CCATTTCTGT ATCTTCACAA AGCTTATTTG TAAATTACAT ACATGCCCTG    60

ATG GAC CCA TCC ATG GAT CTA CCG ACG ACC ACC GAA TCA CCG ACG TTT    108
Met Asp Pro Ser Met Asp Leu Pro Thr Thr Thr Glu Ser Pro Thr Phe
  1               5                  10                  15

AAC TCA GCT CAA GTT GTA AAC CAT GCT CCT ACC CCT ACC CCT CCT CAA    156
Asn Ser Ala Gln Val Val Asn His Ala Pro Thr Pro Thr Pro Pro Gln
             20                  25                  30

CCC CCT CCC CCT GCC CCT TCC TTT TCG CCT ACC CAC CCG CCT TAT GCT    204
Pro Pro Pro Pro Ala Pro Ser Phe Ser Pro Thr His Pro Pro Tyr Ala
         35                  40                  45

GAG ATG ATA ACG GCG GCG ATA ACG GCG TTA AAG GAG AGG GAT GGG TCA    252
Glu Met Ile Thr Ala Ala Ile Thr Ala Leu Lys Glu Arg Asp Gly Ser
     50                  55                  60

AGC AGG ATA GCC ATA GCT AAG TAC ATA GAC CGA GTC TAC ACA AAT CTT    300
Ser Arg Ile Ala Ile Ala Lys Tyr Ile Asp Arg Val Tyr Thr Asn Leu
 65                  70                  75                  80

CCA CCG AAT CAC TCG GCC CTG TTG ACT CAC CAT CTT AAG CGT TTG AAG    348
Pro Pro Asn His Ser Ala Leu Leu Thr His His Leu Lys Arg Leu Lys
                 85                  90                  95

AAC AGT GGT TAC CTT GCT ATG GTC AAA CAC TCT TAC ATG CTC GCC GGA    396
Asn Ser Gly Tyr Leu Ala Met Val Lys His Ser Tyr Met Leu Ala Gly
            100                 105                 110

CCA CCT GGA TCT GCT CCT CCG CCT CCT TCC GCC GAC GCC GAT TCC AAC    444
Pro Pro Gly Ser Ala Pro Pro Pro Pro Ser Ala Asp Ala Asp Ser Asn
        115                 120                 125

GGT GTT GGT ACT GAT GTT TCT TCT CTT TCT AAA AGG AAA CCT GGT CGT    492
Gly Val Gly Thr Asp Val Ser Ser Leu Ser Lys Arg Lys Pro Gly Arg
    130                 135                 140

CCT CCT AAG CTC AAG CCT GAG GCC CAA CCT CAT GCT CAG CCT CAA GTC    540
Pro Pro Lys Leu Lys Pro Glu Ala Gln Pro His Ala Gln Pro Gln Val
145                 150                 155                 160

CAA GCT CAA GTC CAA TTT CAA GAC CAA TTC CAA GCT CAG CTT CAA GCC    588
Gln Ala Gln Val Gln Phe Gln Asp Gln Phe Gln Ala Gln Leu Gln Ala
```

-continued

```
                    165                 170                 175
CAG CTT CAA GCC CAA CTT CAA GCC CAA CAG CAG CAA GCA GCC CAG TTT         636
Gln Leu Gln Ala Gln Leu Gln Ala Gln Gln Gln Gln Ala Ala Gln Phe
            180                 185                 190

CAA CCT CAA TTC CAA CTC ATC CAA CAA CAG CCC CAG TAC TTA CCT CAA         684
Gln Pro Gln Phe Gln Leu Ile Gln Gln Gln Pro Gln Tyr Leu Pro Gln
            195                 200                 205

CAA CAG TTC CAG CCC GAC CCA TTA CTC CAA CCT CAG CAA CAG TTC CAG         732
Gln Gln Phe Gln Pro Asp Pro Leu Leu Gln Pro Gln Gln Gln Phe Gln
            210                 215                 220

ACC CAG CCA CAG ACG CAG GCC TAT GCT ACT CCT GAA GGC CAT AAT TAT         780
Thr Gln Pro Gln Thr Gln Ala Tyr Ala Thr Pro Glu Gly His Asn Tyr
225                 230                 235                 240

GCT GGC CTT GGC GCT GAA TCC GTG TTT GTT TCT CTT GGG CTA GCT GAT         828
Ala Gly Leu Gly Ala Glu Ser Val Phe Val Ser Leu Gly Leu Ala Asp
                245                 250                 255

GGG CCT GTT GGA GTT CAG AAT CCT GCT GTT GGG CTG GCT CCG GCA CCG         876
Gly Pro Val Gly Val Gln Asn Pro Ala Val Gly Leu Ala Pro Ala Pro
            260                 265                 270

GGA GCT GAA GAG AGT ACG GCA AAG AGA CGA CCA GGT CGT CCC CGT AAG         924
Gly Ala Glu Glu Ser Thr Ala Lys Arg Arg Pro Gly Arg Pro Arg Lys
            275                 280                 285

GAT GGT TCC ACT GTG GTT AAA CCG GTG GAA CCC AAA TTA CCG GAC CAG         972
Asp Gly Ser Thr Val Val Lys Pro Val Glu Pro Lys Leu Pro Asp Gln
290                 295                 300

AGC GGT GGT AGT AAG AGG AGA CCT GGT CGT CCT CCT AAG AGT GTG ACA        1020
Ser Gly Gly Ser Lys Arg Arg Pro Gly Arg Pro Pro Lys Ser Val Thr
305                 310                 315                 320

GTT AAT GCT GCT CCT GGA TCA GCT ATG GGT TCT GGA CGA CGA GGT CGG        1068
Val Asn Ala Ala Pro Gly Ser Ala Met Gly Ser Gly Arg Arg Gly Arg
                325                 330                 335

CCC AGG AAA AAT TCT GTT CCT GGA CGA CGA GGT CGG CCC AGG AAG AAT        1116
Pro Arg Lys Asn Ser Val Pro Gly Arg Arg Gly Arg Pro Arg Lys Asn
            340                 345                 350

GCG GCT GTT GCT GCT GCC AAT GGC GGT GCC AAT GTC GCA AAT ATT CCT        1164
Ala Ala Val Ala Ala Ala Asn Gly Gly Ala Asn Val Ala Asn Ile Pro
            355                 360                 365

TCT GTT GGT GCC AAT GTG ACC AAT GTT CCA GCT GGT GGT GTC CCG GGA        1212
Ser Val Gly Ala Asn Val Thr Asn Val Pro Ala Gly Gly Val Pro Gly
            370                 375                 380

GCC ATA ACA ACA CCT AAA CGA AGG GGA CGG CCA CCA AGG TCT AGT GGA        1260
Ala Ile Thr Thr Pro Lys Arg Arg Gly Arg Pro Pro Arg Ser Ser Gly
385                 390                 395                 400

CCT CCT GCT GCT ACT GTG GGT GTT ACA GAT GTG CCT ATT GCT GCT GCT        1308
Pro Pro Ala Ala Thr Val Gly Val Thr Asp Val Pro Ile Ala Ala Ala
                405                 410                 415

TTT GAT ACG GAA AAC TTG CCT AAT GCT GTT GGT GGT GGC GGT GTC ACA        1356
Phe Asp Thr Glu Asn Leu Pro Asn Ala Val Gly Gly Gly Gly Val Thr
            420                 425                 430

AAT AAT GGG GCT CTG CCT CCC CTC GGA AAG CGA CGT GGA CGG CCT CCA        1404
Asn Asn Gly Ala Leu Pro Pro Leu Gly Lys Arg Arg Gly Arg Pro Pro
            435                 440                 445

AAA TCT TAC GGC GCT GCA GCC GCT GCT CCT ACT GTT AAG AGA CCC AGG        1452
Lys Ser Tyr Gly Ala Ala Ala Ala Ala Pro Thr Val Lys Arg Pro Arg
450                 455                 460

AAG CTT TCT GGA AAA CCT CTG GGT CGA CCT AGA AAG AAT GTG ACA TCC        1500
Lys Leu Ser Gly Lys Pro Leu Gly Arg Pro Arg Lys Asn Val Thr Ser
465                 470                 475                 480

CCT GCA GTT TCG GAC CCC AAG TTG GTG GTG GCC TAT GAA GAG CTA AAG        1548
```

```
Pro Ala Val Ser Asp Pro Lys Leu Val Val Ala Tyr Glu Glu Leu Lys
            485                 490                 495

GGG AAA CTT GAA CAC ATG CAA TCA AGA ATC AAG GAA GCA GCG AAT GCG      1596
Gly Lys Leu Glu His Met Gln Ser Arg Ile Lys Glu Ala Ala Asn Ala
            500                 505                 510

CTG AAG CCA TGC TTA AAT GCT GAA TCG CCA GCA ATT GCT CTG GCA GCA      1644
Leu Lys Pro Cys Leu Asn Ala Glu Ser Pro Ala Ile Ala Leu Ala Ala
            515                 520                 525

TTG CAA GAG TTA GAA GAG TTA GCA GCA GCA GGG GGG AAT CCA GTG CAG      1692
Leu Gln Glu Leu Glu Glu Leu Ala Ala Ala Gly Gly Asn Pro Val Gln
            530                 535                 540

CAA AAT TGATAAAAGA AGATGTCGCA GAGATTAGGA ATATGGAGGC AGTGCTTAAA       1748
Gln Asn
545

CTCAGAGTGT TAAACATTAT TCAAGGCTGG AAACCATGAA AATCAAGGAA GTTTCGGTGC    1808

AGACTAGTGT TTGTGACAGG ACGAAGATGC GCTTAGACTT GGAGGCAGTG TAGCTACCTA    1868

CCTCTAATGT CAATTTGTTA GGTTAAAGCA GGATTTGATA TTTTGTTGCA CAGTATGAAG    1928

TATGTTTTAG TTCTAACTGT ATTAGCAGTT GATTTCGTCA TTTGATAATT ACCTTATTCT    1988

GCTAATTTGG TTAATGACAA TTAAGGGGGA GACAAAATCA TGCTCGTGGG CTATATGTAC    2048

TGTTGTTTGA GTATGTTGAA TGGATGGAAA TGCCTTTGTT AGATAGATGT ATAATGCCGG    2108

CATTATCCCT CATCAACAGT TGCCTTTGCA AATGTCGTAA AAGCATTTGA ATTTTAT      2165

(2) INFORMATION FOR SEQ ID NO:3:

(i) SEQUENCE CHARACTERISTICS:
        (A) LENGTH: 546 amino acids
        (B) TYPE: amino acid
        (D) TOPOLOGY: linear (ii) MOLECULE TYPE: protein (xi) SEQUENCE DESCRIPTION: SEQ ID NO:3:

Met Asp Pro Ser Met Asp Leu Pro Thr Thr Thr Glu Ser Pro Thr Phe
 1               5                  10                  15

Asn Ser Ala Gln Val Val Asn His Ala Pro Thr Pro Thr Pro Pro Gln
                20                  25                  30

Pro Pro Pro Pro Ala Pro Ser Phe Ser Pro Thr His Pro Pro Tyr Ala
            35                  40                  45

Glu Met Ile Thr Ala Ala Ile Thr Ala Leu Lys Glu Arg Asp Gly Ser
    50                  55                  60

Ser Arg Ile Ala Ile Ala Lys Tyr Ile Asp Arg Val Tyr Thr Asn Leu
65                  70                  75                  80

Pro Pro Asn His Ser Ala Leu Leu Thr His His Leu Lys Arg Leu Lys
                85                  90                  95

Asn Ser Gly Tyr Leu Ala Met Val Lys His Ser Tyr Met Leu Ala Gly
            100                 105                 110

Pro Pro Gly Ser Ala Pro Pro Pro Ser Ala Asp Ala Asp Ser Asn
        115                 120                 125

Gly Val Gly Thr Asp Val Ser Ser Leu Ser Lys Arg Lys Pro Gly Arg
    130                 135                 140

Pro Pro Lys Leu Lys Pro Glu Ala Gln Pro His Ala Gln Pro Gln Val
145                 150                 155                 160

Gln Ala Gln Val Gln Phe Gln Asp Gln Phe Gln Ala Gln Leu Gln Ala
                165                 170                 175

Gln Leu Gln Ala Gln Leu Gln Ala Gln Gln Gln Ala Ala Gln Phe
```

-continued

```
                180                 185                 190
Gln Pro Gln Phe Gln Leu Ile Gln Gln Pro Gln Tyr Leu Pro Gln
            195                 200                 205
Gln Gln Phe Gln Pro Asp Pro Leu Leu Gln Pro Gln Gln Phe Gln
210                 215                 220
Thr Gln Pro Gln Thr Gln Ala Tyr Ala Thr Pro Glu Gly His Asn Tyr
225                 230                 235                 240
Ala Gly Leu Gly Ala Glu Ser Val Phe Val Ser Leu Gly Leu Ala Asp
            245                 250                 255
Gly Pro Val Gly Val Gln Asn Pro Ala Val Gly Leu Ala Pro Ala Pro
            260                 265                 270
Gly Ala Glu Glu Ser Thr Ala Lys Arg Arg Pro Gly Arg Pro Arg Lys
            275                 280                 285
Asp Gly Ser Thr Val Val Lys Pro Val Glu Pro Lys Leu Pro Asp Gln
290                 295                 300
Ser Gly Gly Ser Lys Arg Arg Pro Gly Arg Pro Pro Lys Ser Val Thr
305                 310                 315                 320
Val Asn Ala Ala Pro Gly Ser Ala Met Gly Ser Gly Arg Arg Gly Arg
            325                 330                 335
Pro Arg Lys Asn Ser Val Pro Gly Arg Arg Gly Arg Pro Arg Lys Asn
            340                 345                 350
Ala Ala Val Ala Ala Asn Gly Gly Ala Asn Val Ala Asn Ile Pro
            355                 360                 365
Ser Val Gly Ala Asn Val Thr Asn Val Pro Ala Gly Gly Val Pro Gly
            370                 375                 380
Ala Ile Thr Thr Pro Lys Arg Arg Gly Arg Pro Pro Arg Ser Ser Gly
385                 390                 395                 400
Pro Pro Ala Ala Thr Val Gly Val Thr Asp Val Pro Ile Ala Ala Ala
            405                 410                 415
Phe Asp Thr Glu Asn Leu Pro Asn Ala Val Gly Gly Gly Val Thr
            420                 425                 430
Asn Asn Gly Ala Leu Pro Pro Leu Gly Lys Arg Arg Gly Arg Pro Pro
            435                 440                 445
Lys Ser Tyr Gly Ala Ala Ala Ala Pro Thr Val Lys Arg Pro Arg
450                 455                 460
Lys Leu Ser Gly Lys Pro Leu Gly Arg Pro Arg Lys Asn Val Thr Ser
465                 470                 475                 480
Pro Ala Val Ser Asp Pro Lys Leu Val Val Ala Tyr Glu Glu Leu Lys
            485                 490                 495
Gly Lys Leu Glu His Met Gln Ser Arg Ile Lys Glu Ala Ala Asn Ala
            500                 505                 510
Leu Lys Pro Cys Leu Asn Ala Glu Ser Pro Ala Ile Ala Leu Ala Ala
            515                 520                 525
Leu Gln Glu Leu Glu Glu Leu Ala Ala Gly Gly Asn Pro Val Gln
            530                 535                 540
Gln Asn
545
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

CATAAGGATT AGGAATTTAA TTTCGTAG                                      28

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

TATATATATA TATATATATA TATATATATA CCACGT                             36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:6:

CTTGTCATTA TTTCTCCACC ACCCCCTTCA CTTCCC                             36

(2) INFORMATION FOR SEQ ID NO:7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:7:

TGCAGGTGTT GCACGTGATA CTCACCTACC CTGCA                              35

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

CGACTCACCT ACCTGACATG CTACGCAGCG                                    30

(2) INFORMATION FOR SEQ ID NO:9:

(i) SEQUENCE CHARACTERISTICS:
        (A) LENGTH: 98 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:9:

```
Pro Xaa Ala Ala His Pro Xaa Ala Ala Tyr Xaa Ala Ala Glu Met Ile
1               5                   10                  15

Xaa Ala Ala Ala Ile Xaa Ala Ala Leu Lys Glu Arg Xaa Ala Ala Gly
            20                  25                  30

Ser Ser Xaa Ala Ala Ala Ile Xaa Ala Ala Lys Xaa Ala Ala Ile Xaa
        35                  40                  45
```

```
Ala Ala Leu Pro Pro Xaa Ala Ala Leu Leu Xaa Ala Ala Leu Lys Arg
     50              55                  60

Leu Xaa Ala Ala Ser Xaa Ala Ala Leu Xaa Ala Ala Val Lys Xaa Ala
65               70              75                       80

Ala Ser Xaa Ala Ala Xaa Ala Ala Pro Xaa Ala Ala Pro Xaa Ala
             85              90                  95

Ala Ala
```

(2) INFORMATION FOR SEQ ID NO:10:

(i) SEQUENCE CHARACTERISTICS:
        (A) LENGTH: 95 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:10:

```
Pro Xaa Ala Ala Ser Xaa Ala Ala Pro Thr His Pro Pro Tyr Xaa Ala
1                5               10              15

Ala Glu Met Ile Xaa Ala Ala Ala Ile Xaa Ala Ala Leu Lys Glu Arg
             20              25              30

Xaa Ala Ala Gly Ser Ser Xaa Ala Ala Ala Ile Xaa Ala Ala Lys Xaa
             35              40              45

Ala Ala Ile Xaa Ala Ala Leu Pro Xaa Ala Ala Asn Xaa Ala Ala Leu
     50              55              60

Leu Xaa Ala Ala Leu Lys Xaa Ala Ala Ser Xaa Ala Ala Leu Xaa Ala
65               70              75                       80

Ala Val Lys Xaa Ala Ala Ser Tyr Xaa Ala Ala Leu Xaa Ala Ala
             85              90                  95
```

(2) INFORMATION FOR SEQ ID NO:11:

(i) SEQUENCE CHARACTERISTICS:
        (A) LENGTH: 98 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:11:

```
Xaa Ala Ala His Pro Xaa Ala Ala Tyr Xaa Ala Ala Glu Met Ile Xaa
1                5               10              15

Ala Ala Ala Ile Xaa Ala Ala Leu Lys Glu Arg Xaa Ala Ala Gly Ser
             20              25              30

Ser Xaa Ala Ala Ala Ile Xaa Ala Ala Lys Xaa Ala Ala Ile Xaa Ala
         35              40              45

Ala Leu Pro Pro Xaa Ala Ala Leu Leu Xaa Ala Ala Leu Lys Arg Leu
     50              55              60

Xaa Ala Ala Ser Gly Xaa Ala Ala Leu Xaa Ala Ala Val Lys Xaa Ala
65               70              75                       80

Ala Ser Xaa Ala Ala Leu Xaa Ala Ala Ala Xaa Ala Ala Pro Xaa Ala
             85              90                  95

Ala Ala
```

(2) INFORMATION FOR SEQ ID NO:12:

(i) SEQUENCE CHARACTERISTICS:

(A) LENGTH: 98 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:12:

Xaa Ala Ala His Pro Xaa Ala Ala Tyr Xaa Ala Ala Glu Met Ile Xaa
1               5                   10                  15

Ala Ala Ala Ile Xaa Ala Ala Leu Lys Glu Arg Xaa Ala Ala Gly Ser
                20                  25                  30

Ser Xaa Ala Ala Ile Xaa Ala Ala Lys Xaa Ala Ala Ile Xaa Ala
        35                  40                  45

Ala Leu Leu Pro Xaa Ala Ala Leu Leu Xaa Ala Ala Leu Lys Arg Leu
    50                  55                  60

Xaa Ala Ala Ser Gly Xaa Ala Ala Leu Xaa Ala Ala Val Lys Xaa Ala
65                  70                  75                  80

Ala Ser Xaa Ala Ala Leu Xaa Ala Ala Xaa Ala Ala Pro Xaa Ala
            85                  90                  95

Ala Ala (2) INFORMATION FOR SEQ ID NO:13:

(i) SEQUENCE CHARACTERISTICS:
        (A) LENGTH: 91 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:13:

Xaa Ala Ala Pro Xaa Ala Ala His Pro Xaa Ala Ala Tyr Xaa Ala Ala
1               5                   10                  15

Glu Met Ile Xaa Ala Ala Ala Ile Xaa Ala Ala Leu Lys Glu Xaa Ala
                20                  25                  30

Ala Gly Ser Ser Xaa Ala Ala Ala Ile Ala Lys Xaa Ala Ala Ile Xaa
                35                  40                  45

Ala Ala Leu Pro Xaa Ala Ala Asn Xaa Ala Ala Leu Leu Xaa Ala Ala
    50                  55                  60

Leu Lys Xaa Ala Ala Ser Gly Xaa Ala Ala Leu Xaa Ala Ala Val Lys
65                  70                  75                  80

Xaa Ala Ala Ser Xaa Ala Ala Leu Xaa Ala Ala
            85                  90

(2) INFORMATION FOR SEQ ID NO:14:

(i) SEQUENCE CHARACTERISTICS:
        (A) LENGTH: 53 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:14:

Xaa Ala Ala Pro Xaa Ala Ala Pro Thr His Pro Pro Tyr Xaa Ala Ala
1               5                   10                  15

Glu Met Xaa Ala Ala Ala Ile Thr Xaa Ala Ala Leu Lys Glu Arg Xaa
                20                  25                  30

```
Ala Ala Gly Ser Ser Xaa Ala Ala Xaa Ala Ala Lys Xaa Ala Ala
            35                  40                  45

Ile Xaa Ala Ala Tyr
    50
```

(2) INFORMATION FOR SEQ ID NO:15:

(i) SEQUENCE CHARACTERISTICS:
        (A) LENGTH: 48 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:15:

```
Xaa Ala Ala Pro Xaa Ala Ala Ser Pro Thr His Xaa Ala Ala Pro Tyr
1               5                   10                  15

Ala Glu Met Xaa Ala Ala Ala Ile Thr Xaa Ala Ala Leu Lys Glu Arg
            20                  25                  30

Xaa Ala Ala Gly Ser Ser Xaa Ala Ala Ala Ile Ala Lys Xaa Ala Ala
            35                  40                  45
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:16:

```
Pro Gly Arg Lys Pro Arg Gly Arg Pro Lys Lys
1               5                   10
```

(2) INFORMATION FOR SEQ ID NO:17:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

```
Thr Ala Lys Arg Arg Pro Gly Arg Pro Arg Lys
1               5                   10
```

(2) INFORMATION FOR SEQ ID NO:18:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:18:

```
Gly Ser Lys Arg Arg Pro Gly Arg Pro Pro Lys
1               5                   10
```

(2) INFORMATION FOR SEQ ID NO:19:

```
    (i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:19:

Met Gly Ser Gly Arg Arg Gly Arg Pro Arg Lys
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:20:

Ser Val Pro Gly Arg Arg Gly Arg Pro Arg Lys
1               5                   10

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:21:

Thr Thr Pro Lys Arg Arg Gly Arg Pro Pro Arg
1               5                   10

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:22:

Pro Leu Gly Lys Arg Arg Gly Arg Pro Pro Lys
1               5                   10
```